(12) United States Patent
Madjarov et al.

(10) Patent No.: US 10,070,904 B2
(45) Date of Patent: Sep. 11, 2018

(54) BONE FIXATION IMPLANTS

(71) Applicant: Jeko Metodiev Madjarov, Charlotte, NC (US)

(72) Inventors: Jeko Metodiev Madjarov, Charlotte, NC (US); Sophia Jekova Madjarova, Charlotte, NC (US); Svetozar Madzharov, Charlotte, NC (US)

( * ) Notice: Subject to any disclaimer, the term of this patent is extended or adjusted under 35 U.S.C. 154(b) by 599 days.

(21) Appl. No.: 14/626,437

(22) Filed: Feb. 19, 2015

(65) Prior Publication Data

US 2015/0238237 A1 Aug. 27, 2015

Related U.S. Application Data

(60) Provisional application No. 61/942,671, filed on Feb. 21, 2014.

(51) Int. Cl.
*A61B 17/88* (2006.01)
*A61B 17/80* (2006.01)
(Continued)

(52) U.S. Cl.
CPC .......... *A61B 17/80* (2013.01); *A61B 17/842* (2013.01); *A61F 2/44* (2013.01); *A61B 17/8071* (2013.01);
(Continued)

(58) Field of Classification Search
None
See application file for complete search history.

(56) References Cited

U.S. PATENT DOCUMENTS 6,093,201 A * 7/2000 Cooper .................. A61B 17/80
606/232
2010/0036429 A1 2/2010 Buck
(Continued)

FOREIGN PATENT DOCUMENTS

WO WO 2015/003061 A1 1/2015

OTHER PUBLICATIONS

*EVOS Mini Plating System for Small and Long Bones—Smith & Nephew—US Professional* [online] [retrieved May 12, 2015]. Retrieved from the Internet: <URL: http://www.smith-nephew.com/professional/products/all-products/evos-mini/>. 4 pages.
(Continued)

*Primary Examiner* — Sameh Boles
(74) *Attorney, Agent, or Firm* — John P. Zimmer; Nexsen Pruet, PLLC

(57) ABSTRACT

A plating system is described that uses various configurations of bone fixation implants that are configured to be attached to one or more portions of bone. The bone fixation implant may include at least one structural portion (e.g., a wire, plate, mesh, etc.) that includes metal and a polymer body at least partially surrounding the at least one structural portion. The polymer body may define an engaging surface that is configured to engage an attachment member that is applied to the bone fixation implant to fix the bone fixation implant to the bone, such that direct contact between the metal of the structural portion and the attachment member is prevented. Overlying muscle and tissue may be secured to the bone fixation implant to encourage incorporation of the tissue structure into the implant and promote stabilization and healing.

16 Claims, 16 Drawing Sheets

(51) Int. Cl.
  *A61F 2/44* (2006.01)
  *A61B 17/84* (2006.01)
  *A61B 17/56* (2006.01)
  *A61B 17/82* (2006.01)
(52) U.S. Cl.
  CPC ......... *A61B 17/8076* (2013.01); *A61B 17/823* (2013.01); *A61B 2017/564* (2013.01)

(56) References Cited

U.S. PATENT DOCUMENTS

2013/0178906 A1 7/2013 Madjarov
2013/0338719 A1 12/2013 Madjarov
2015/0374497 A1 12/2015 Engstrand et al.

OTHER PUBLICATIONS

International Search Report and Written Opinion corresponding to International Application No. PCT/US2018/030616, conducted by the ISA/US, dated Jul. 20, 2018, 8 pages.

\* cited by examiner

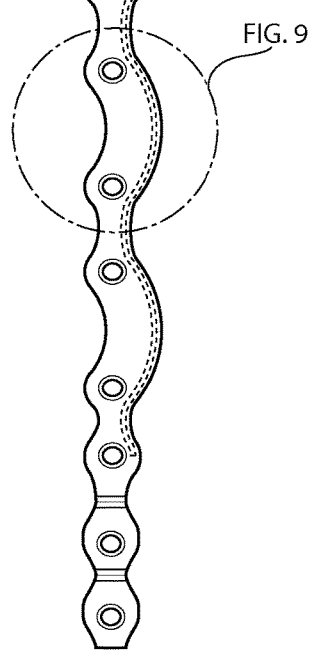
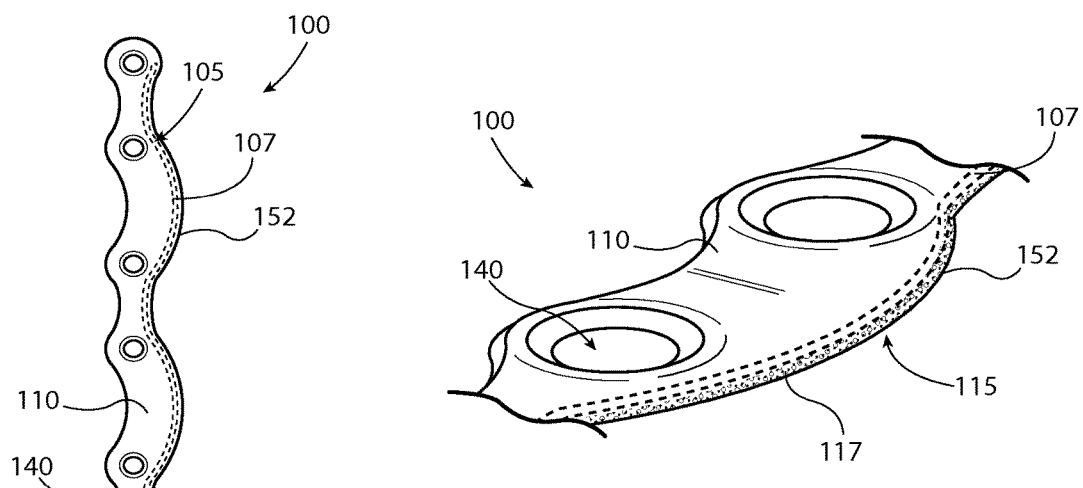
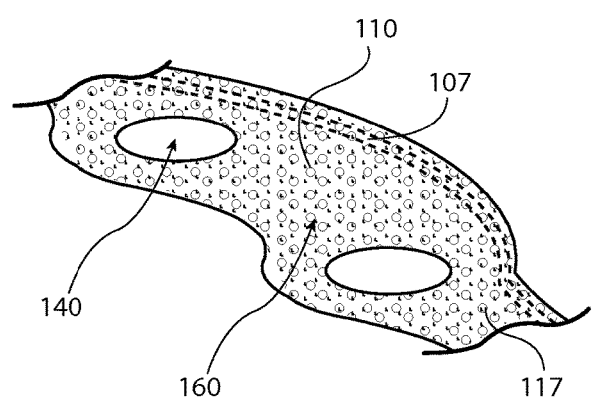
FIG. 8
FIG. 9
FIG. 10

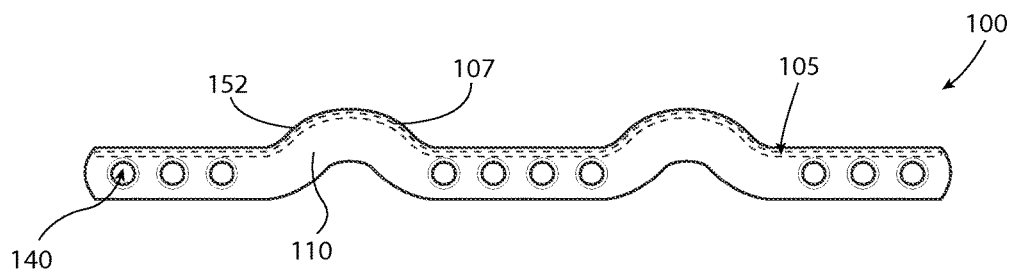
FIG. 11
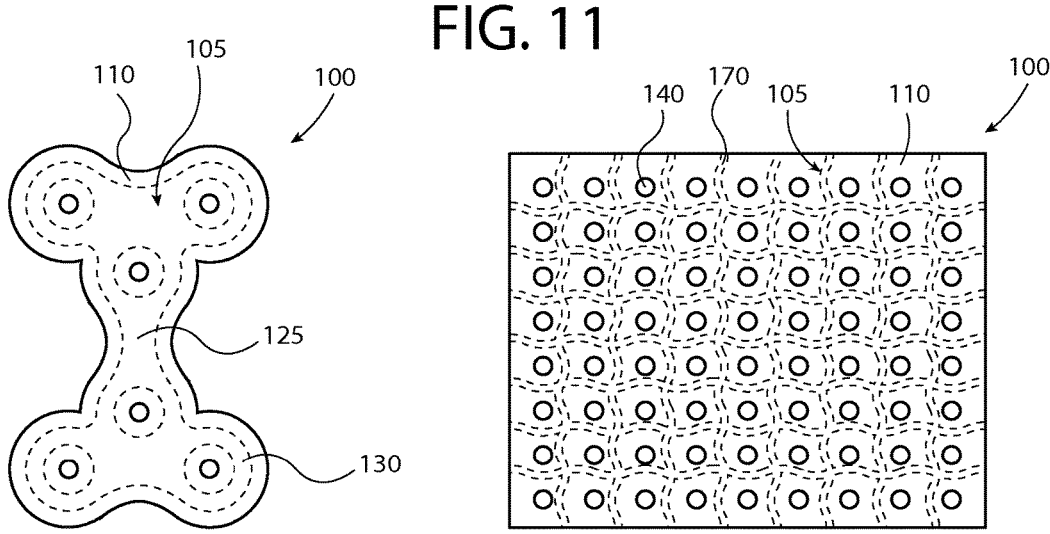
FIG. 12
FIG. 13
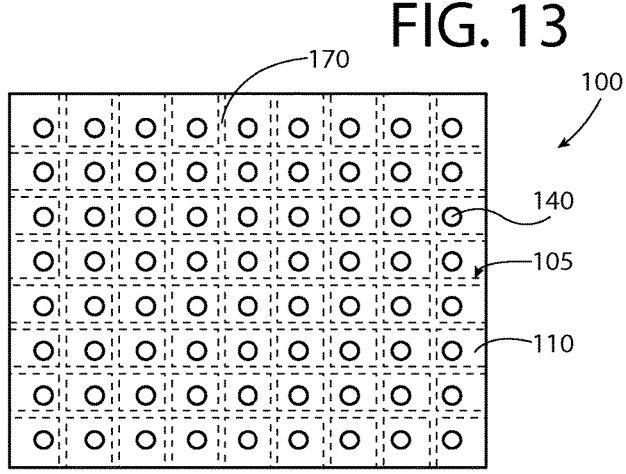
FIG. 14

BONE FIXATION IMPLANTS

CROSS-REFERENCE TO RELATED APPLICATIONS

This application claims the benefit of U.S. Provisional Application No. 61/942,671 entitled "Bone Fixation Implants," filed Feb. 21, 2014, the contents of which are incorporated herein in their entirety.

FIELD OF THE INVENTION

The present invention relates generally to bone fixation implants and methods for supporting and promoting healing of fractured or broken bone, such as ribs, the sternum, facial bones, and spinal bones, among others.

BACKGROUND

Bone fixation implants are used in a variety of medical situations to support broken bones and promote healing. For example, bone fixation implants may be used to replace missing joints, bones, or portions of bone or to support a damaged bone. In particular, one or more bone fixation implants, which may include or be used in conjunction with pins, rods, screws, wires, and/or plates, may be attached to a bone in the area of the fracture to anchor the bone and/or hold portions of the damaged bone together while it heals.

For example, a person who experiences chest trauma due to an accident (e.g., a vehicle collision) may have rib fractures that require the use of bone fixation implants. Implants may also be used to promote healing after surgical procedures, such as a thoracotomy or sternotomy. During a thoracotomy, for example, ribs may be broken by a surgeon to provide access to organs such as the heart and lungs. In a sternotomy, a longitudinal incision may be made along a midline of a patient's sternum, and the two resulting portions of the sternum may be forced apart to allow the surgeon to gain access to the patient's thoracic cavity (e.g., during open heart surgery). A surgeon may use bone fixation implants following such procedures to repair the patient's chest cavity.

In still other cases, bone implants may be used to promote the healing of other bones, such as bones in the face or spine. For example, bone fixation implants may be used during facial plastic surgery and reconstructive surgery to support the healing of bones in the proper configuration. Implants may also be used in neurosurgery of the spine to hold spinal bone portions together during healing.

Accordingly, there is a need for bone fixation implants and methods for supporting and promoting healing of fractured or broken bone that are safe, reproducible, simple to administer, and cause the least amount of pain to the patient.

BRIEF SUMMARY OF EXAMPLE EMBODIMENTS

Embodiments of the present invention, therefore, provide bone fixation implants that can be secured to underlying bone and, at the same time, can be attached to overlying tissue structure to encourage the incorporation of muscle and/or soft tissue into the bone fixation implant and promote stabilization of the bone structure and facilitate healing.

In one embodiment, a bone fixation implant is provided that is configured to be attached to one or more portions of bone. The bone fixation implant may have a bone-engaging surface and a tissue-engaging surface opposite the bone-engaging surface. The bone fixation implant may define a plurality of openings arranged across an overall length and an overall width of the bone fixation implant, and the openings may extend through the bone-engaging surface and the tissue-engaging surface. Each opening may be configured to receive an attachment member for securing the bone fixation implant to an underlying bone structure such that the bone-engaging surface of the bone fixation implant engages the underlying bone structure. Furthermore, the bone fixation implant may be configured to be secured to an overlying tissue structure such that the tissue-engaging surface of the bone fixation implant engages the overlying tissue structure, thereby encouraging incorporation of the tissue structure into the bone fixation implant to promote stabilization of the underlying bone structure during healing.

In some cases, the tissue-engaging surface may comprise a plurality of enclosed channels extending substantially parallel to the bone fixation implant, and each enclosed channel may define a first open end and a second open end. Each enclosed channel may be configured to receive a suturing needle therethrough via the first and second open ends, such that the overlying tissue structure is securable to the bone fixation implant using sutures extending from the tissue structure through at least one of the enclosed channels. The enclosed channels may, in some cases, be arranged at different angles with respect to one another.

In some embodiments, the bone fixation implant may comprise at least one structural portion comprising metal and a polymer body at least partially surrounding the at least one structural portion. The polymer body may define an overall shape of the bone fixation implant comprising the overall width, the overall length, and an overall thickness. The polymer body may define the openings, such that direct contact between the metal of the structural portion and the attachment member is prevented. In some cases, the polymer body may define the bone-engaging surface, the tissue-engaging surface, and the enclosed channels such that direct contact between the metal of the structural portion and any of the bone structure, the tissue-structure, or the sutures is prevented.

In some embodiments, the bone fixation implant may comprise polyether ether ketone (PEEK). For example, in some cases, the polymer body may comprise polyether ether ketone (PEEK), and the structural portion may comprise at least one of titanium, aluminum, stainless steel, or Nitinol. Moreover, in some embodiments, the structural portion may comprise at least one of a wire, a plate, or a mesh.

In some cases, the bone fixation implant may further comprise a plurality of eyelets extending outwardly from the tissue-engaging surface, wherein each eyelet is configured to receive a suturing needle therethrough, such that the overlying tissue structure is securable to the bone fixation implant using sutures extending from the tissue structure through at least one of the eyelets. In still other cases, the bone fixation implant may be configured such that an overall thickness of the bone fixation implant at a rim of each opening is greater than the overall thickness in a region between adjacent openings. In this way, the region between adjacent openings may be configured to receive a suturing needle therethrough, such that the overlying tissue structure is securable to the bone fixation implant using sutures extending from the tissue structure through one or more of the regions.

To promote engagement of the bone-engaging surface and the tissue-engaging surface to the underlying bone structure and the overlying tissue structure, respectively, at least one of the bone-engaging surface or the tissue-engaging surface may define a texture that is configured to enhance engagement of the bone fixation implant with the underlying bone structure and/or the overlying tissue structure, respectively.

Embodiments of a method of fixating bone are also provided herein. In one embodiment, the method may include applying a bone fixation implant to at least one portion of bone, wherein the bone fixation implant has a bone-engaging surface and a tissue-engaging surface opposite the bone-engaging surface. The bone fixation implant may define a plurality of openings arranged across an overall length and an overall width of the bone fixation implant and extending through the bone-engaging surface and the tissue-engaging surface. An attachment member may be inserted into a respective one of the openings to secure the bone fixation implant to an underlying bone structure such that the bone-engaging surface of the bone fixation implant engages the underlying bone structure. In addition, an overlying tissue structure may be sutured to the bone fixation implant such that the tissue-engaging surface of the bone fixation implant engages the overlying tissue structure, thereby encouraging incorporation of the tissue structure into the bone fixation implant to promote stabilization of the underlying bone structure during healing.

In some cases, an overall shape of the bone fixation implant may be modified by cutting off a portion of the bone fixation implant to correspond to a shape of an area of the underlying bone structure to be treated. Additionally or alternatively, the tissue-engaging surface may comprise one of (a) a plurality of enclosed channels extending substantially parallel to the bone fixation implant or (b) a plurality of eyelets extending outwardly from the tissue-engaging surface, and suturing the overlying tissue structure to the bone fixation implant may comprise passing a suturing needle through the overlying tissue structure and at least some of the enclosed channels or the eyelets, respectively.

In some embodiments, the overlying tissue structure may be sutured to the bone fixation implant by passing a suturing needle through a region of the bone fixation implant between adjacent openings, wherein an overall thickness of the bone fixation implant at a rim of each opening is greater than the overall thickness in the region between adjacent openings.

In some cases, inserting the attachment member into the respective one of the openings may comprise thoroscopically monitoring the attachment member as it is inserted.

BRIEF DESCRIPTION OF THE DRAWINGS

Figure 1:
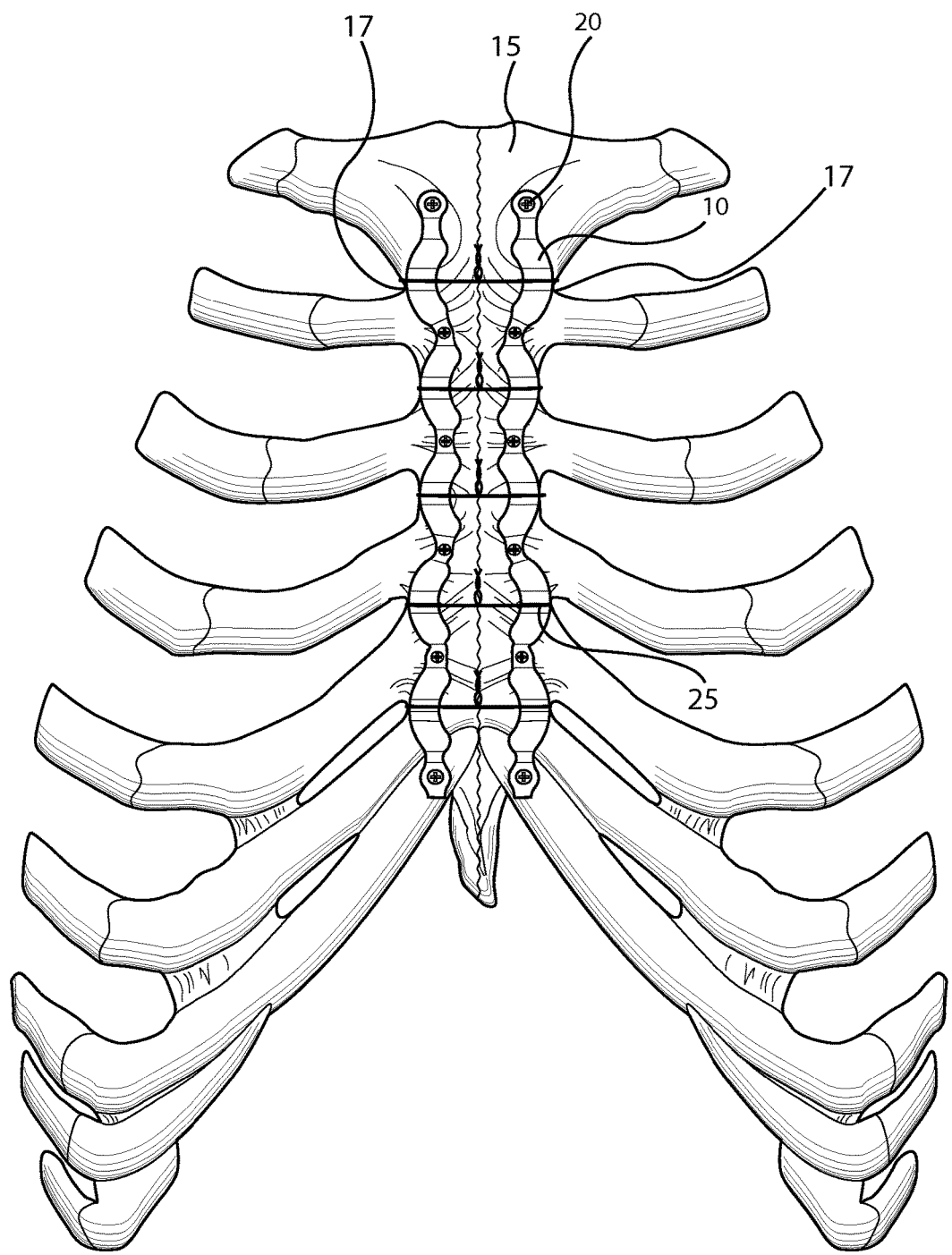
Figure 2:
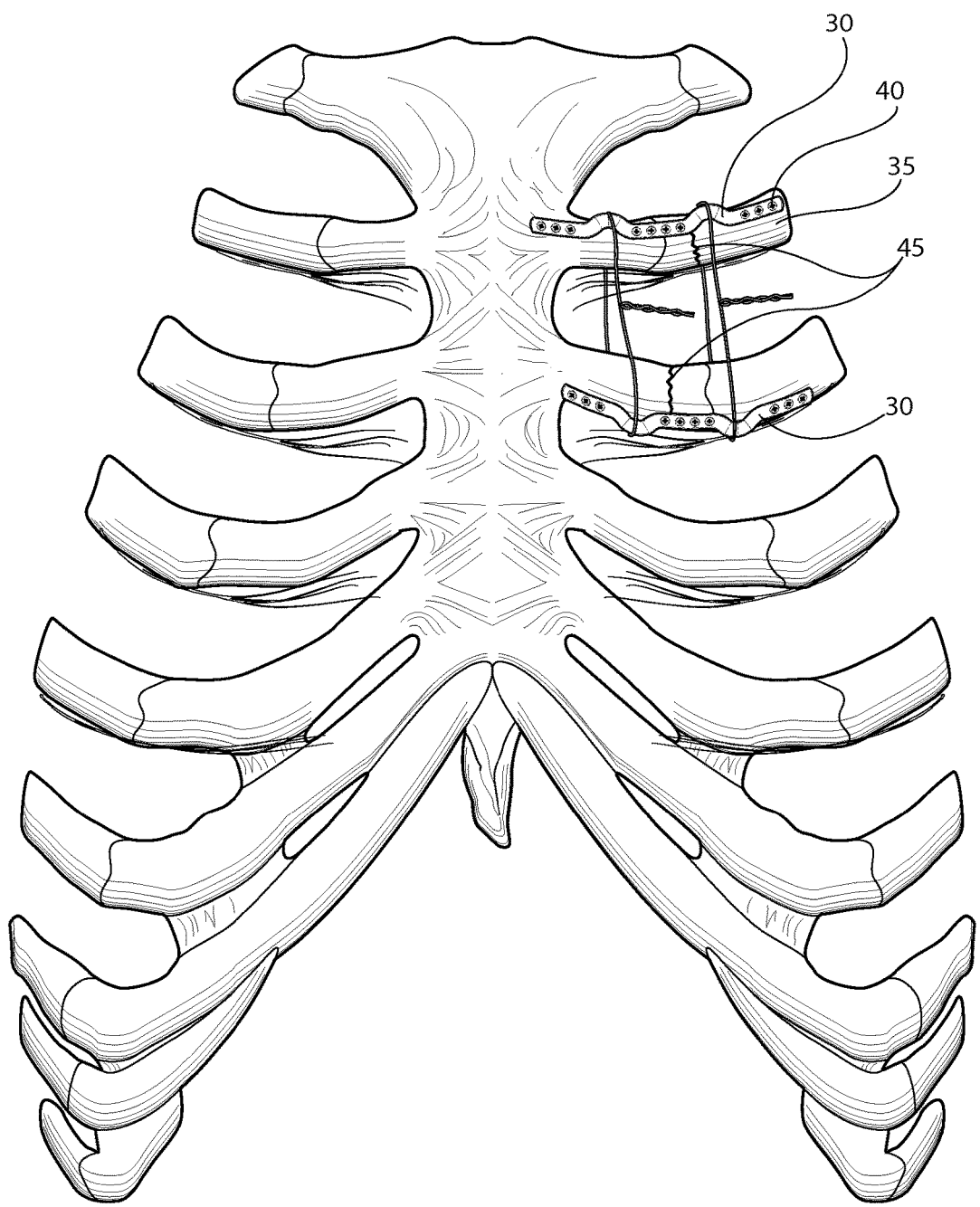
Figure 3:
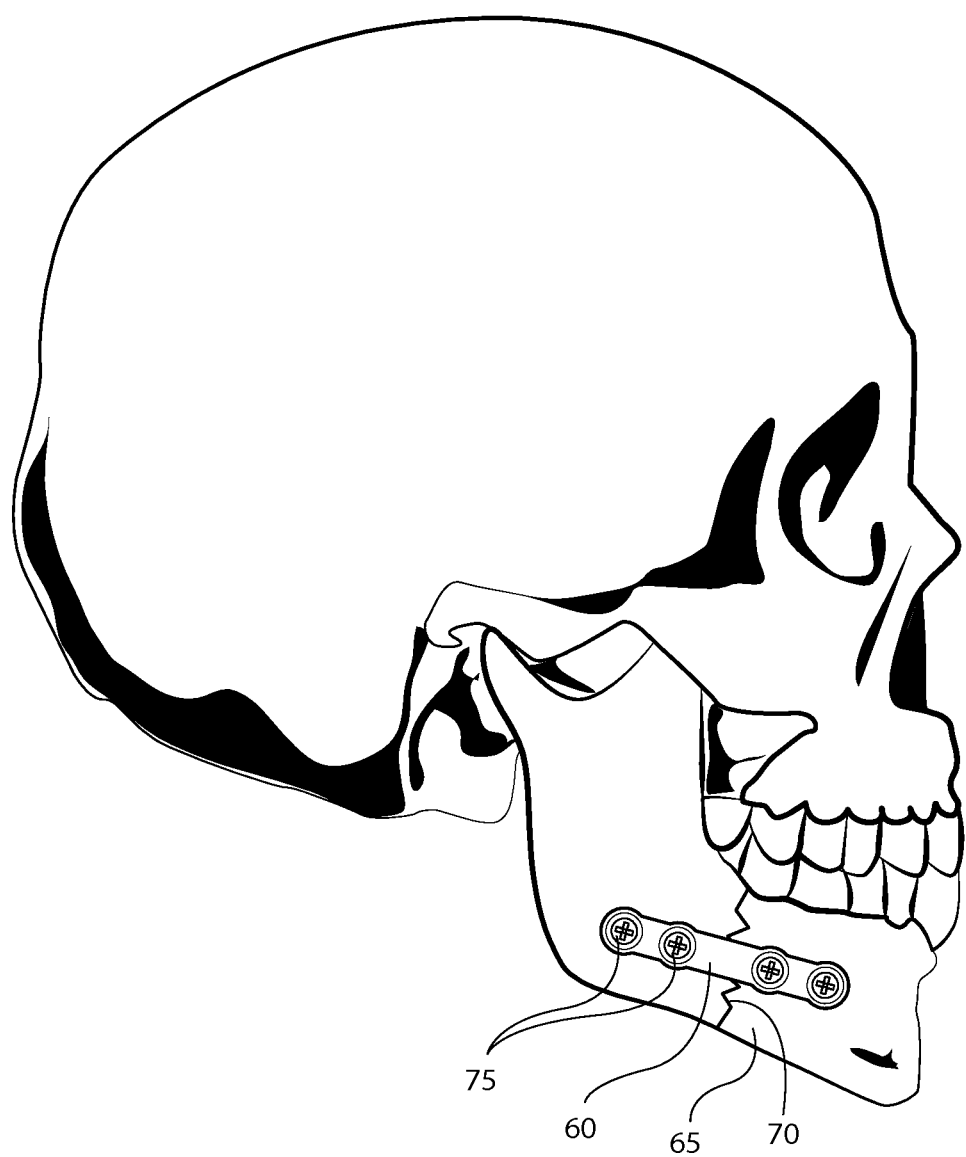
Figure 4:
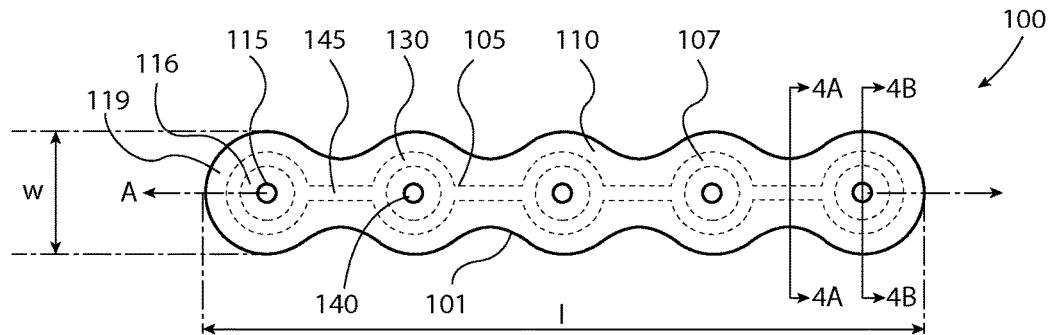
Figure 4A:
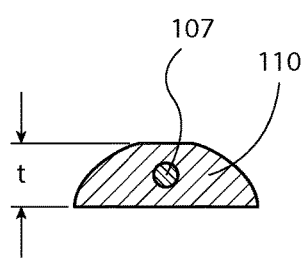
Figure 4B:
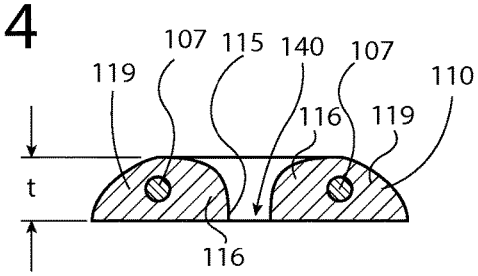
Figure 4C:
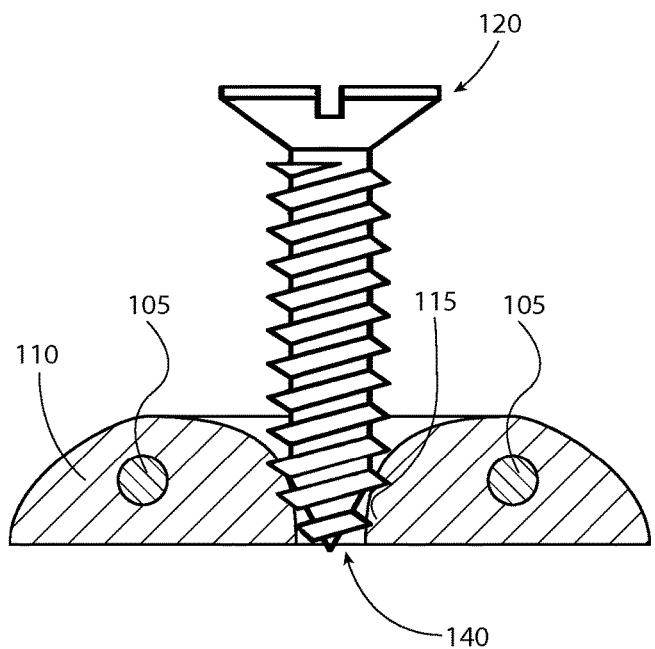
Figure 5:
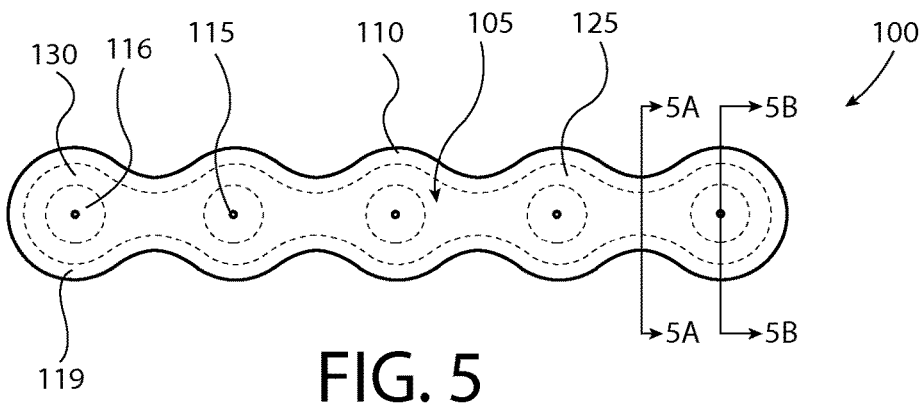
Figure 5A:
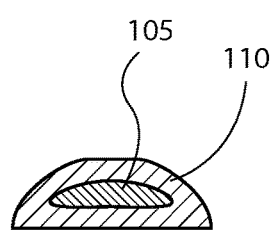
Figure 5B:
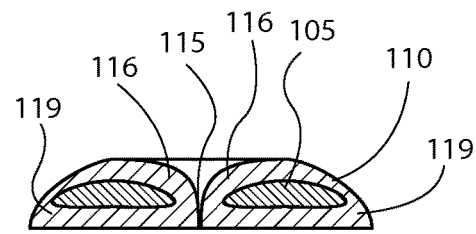
Figure 6:
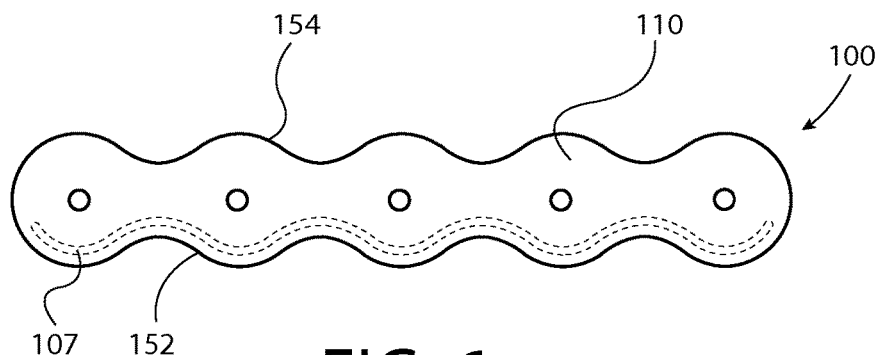
Figure 6A:
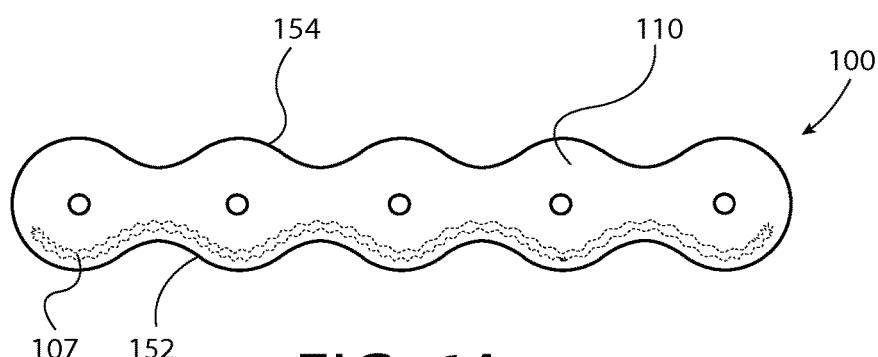
Figure 7:
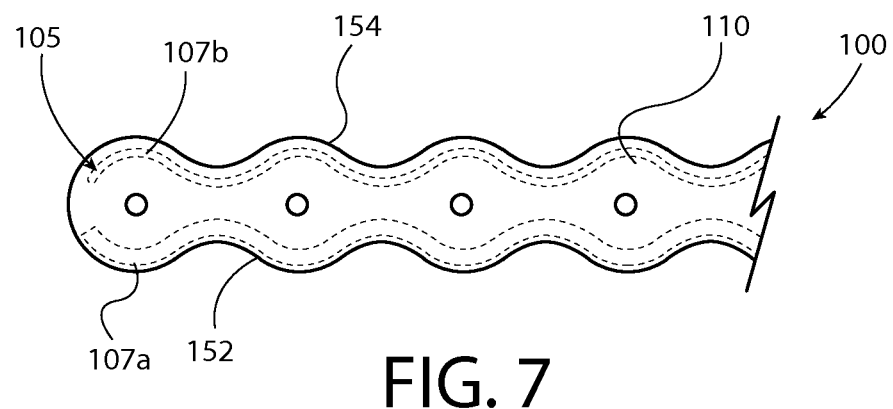
Figure 7A:
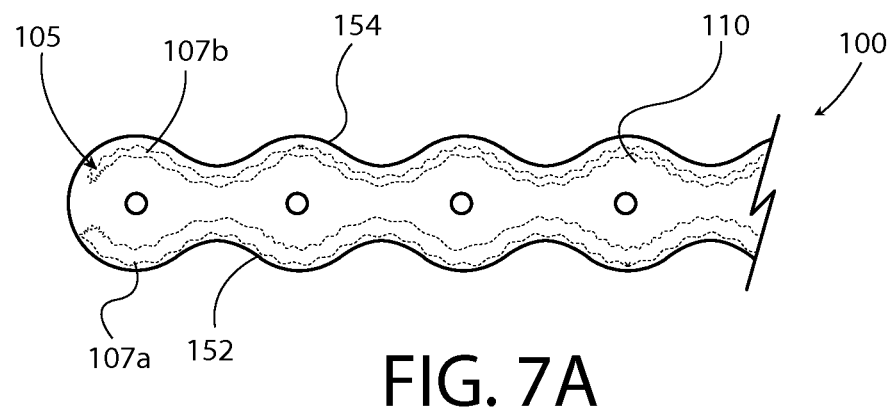
Figure 15:
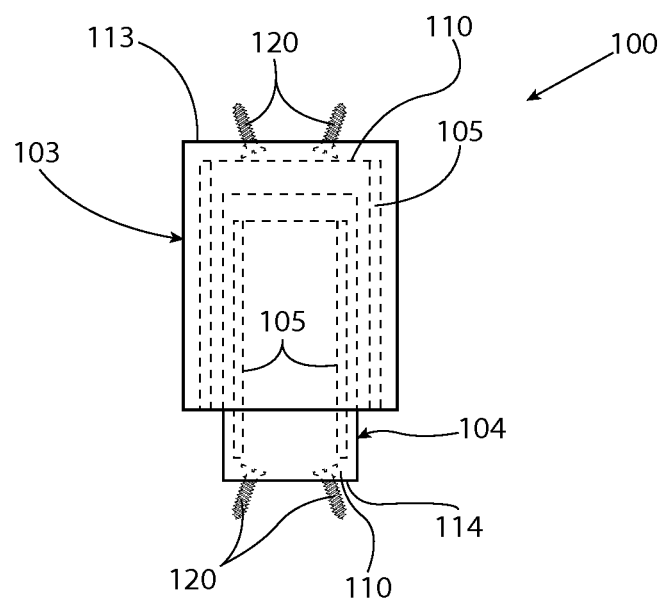
Figure 16:
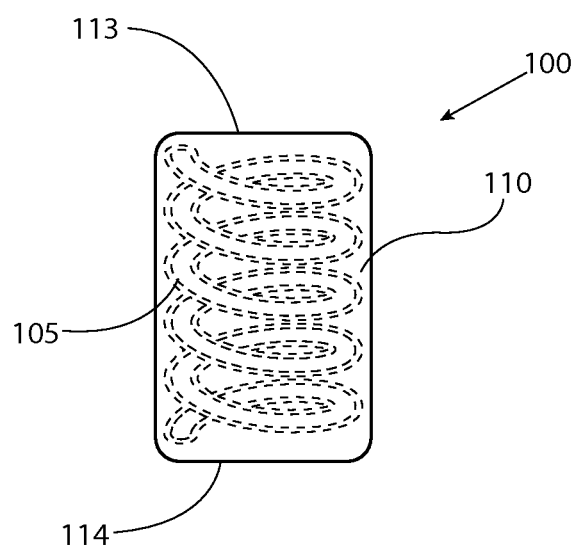
Figure 17:
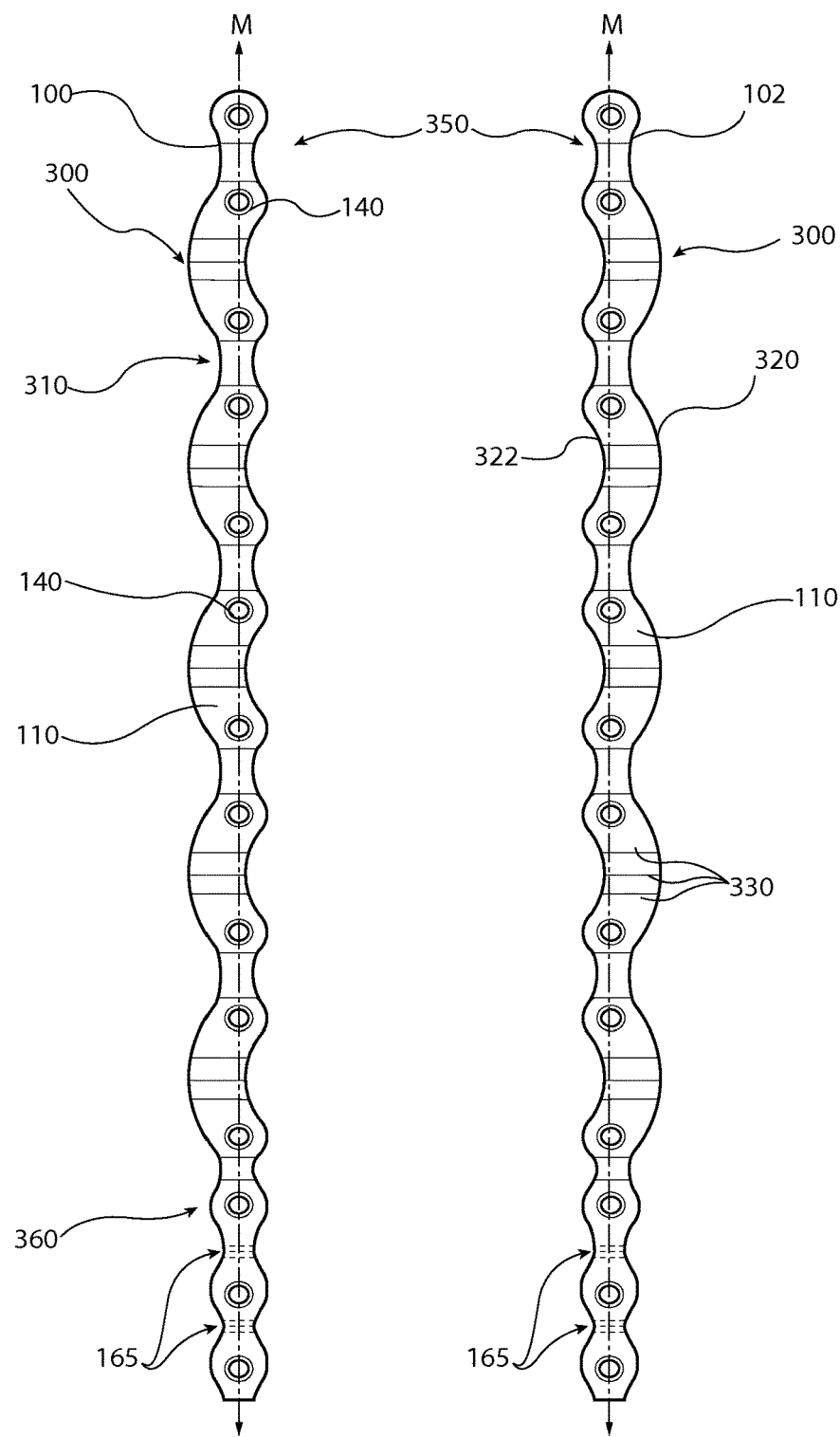
Figure 18:
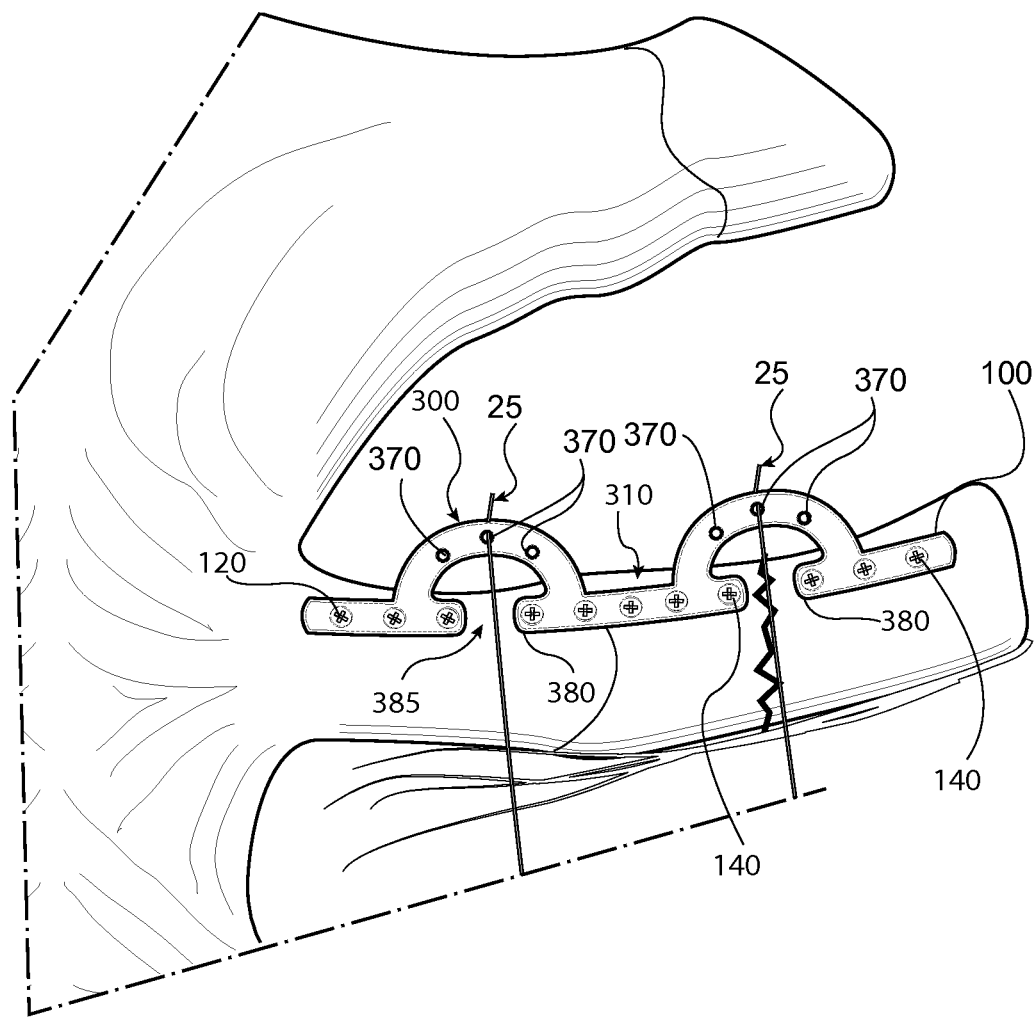
Figure 19:
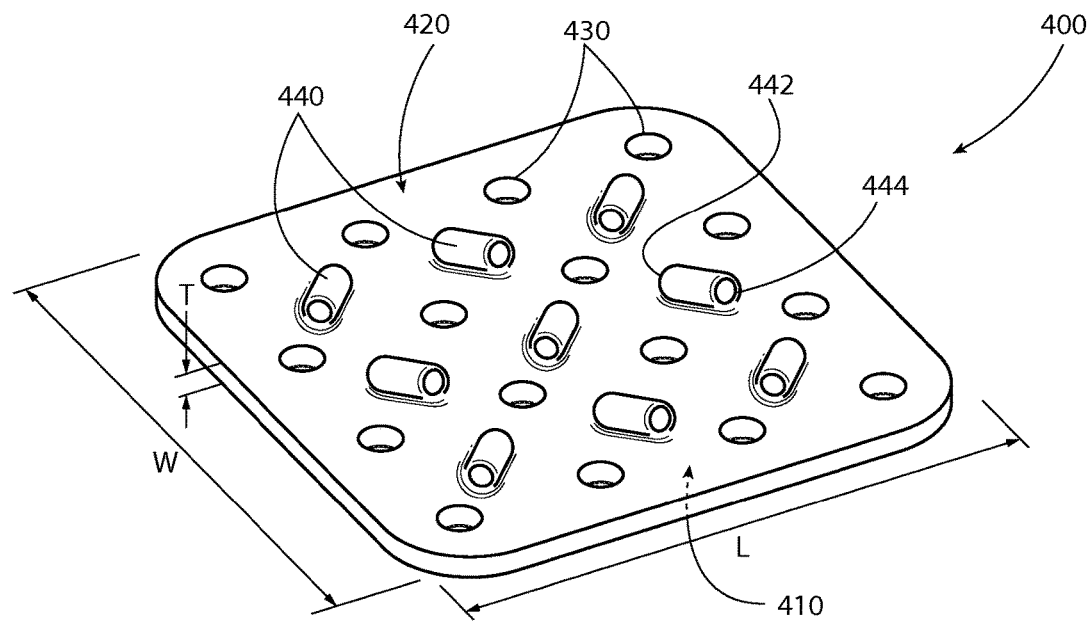
Figure 20:
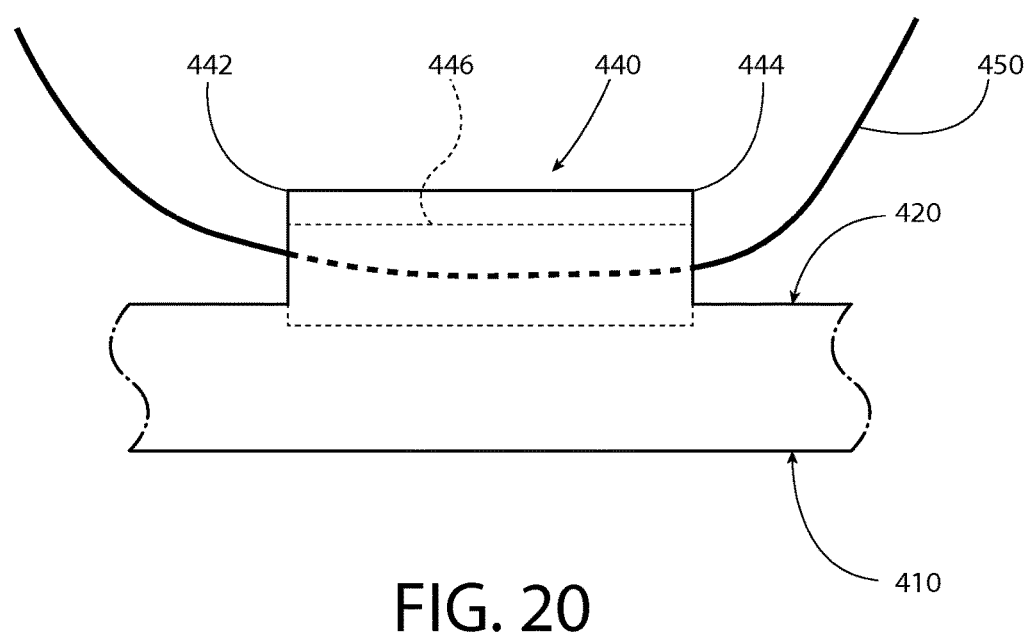
Figure 21:
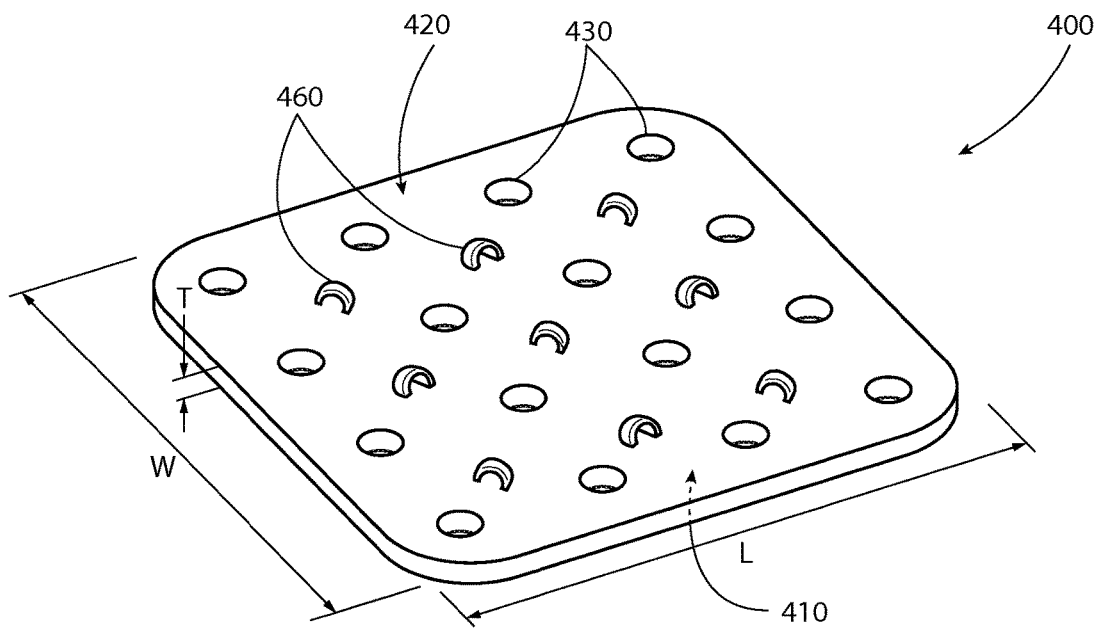
Figure 22:
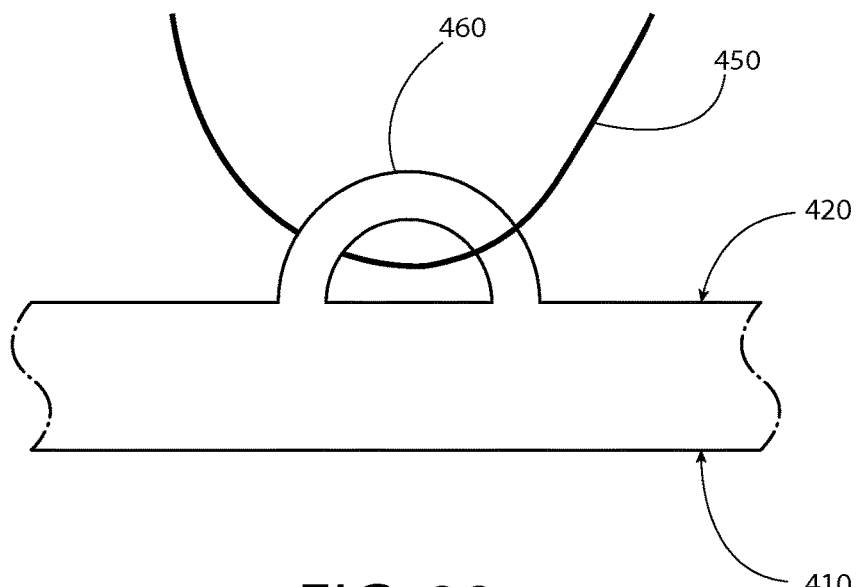
Figure 23:
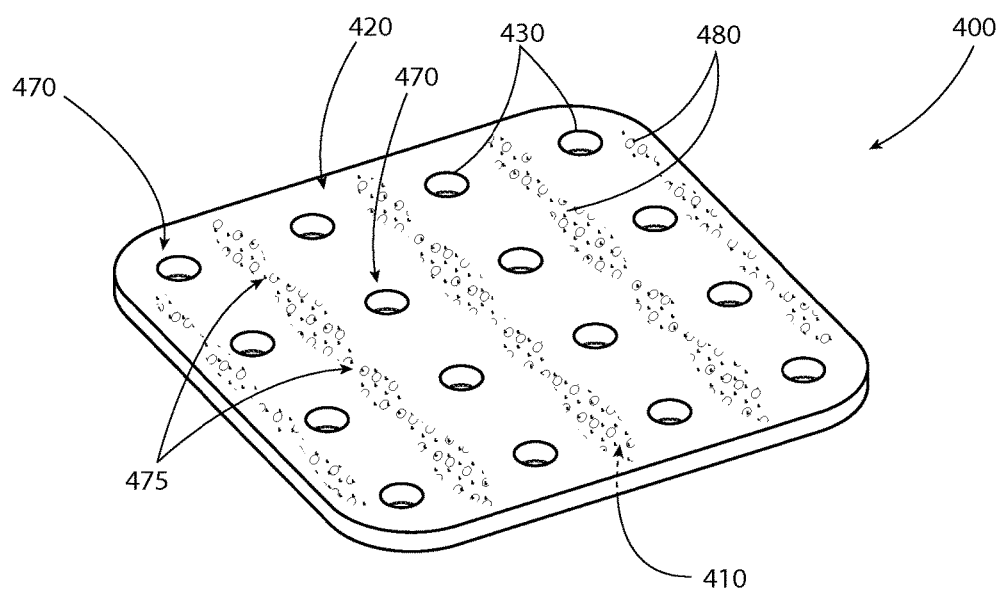
Figure 24:
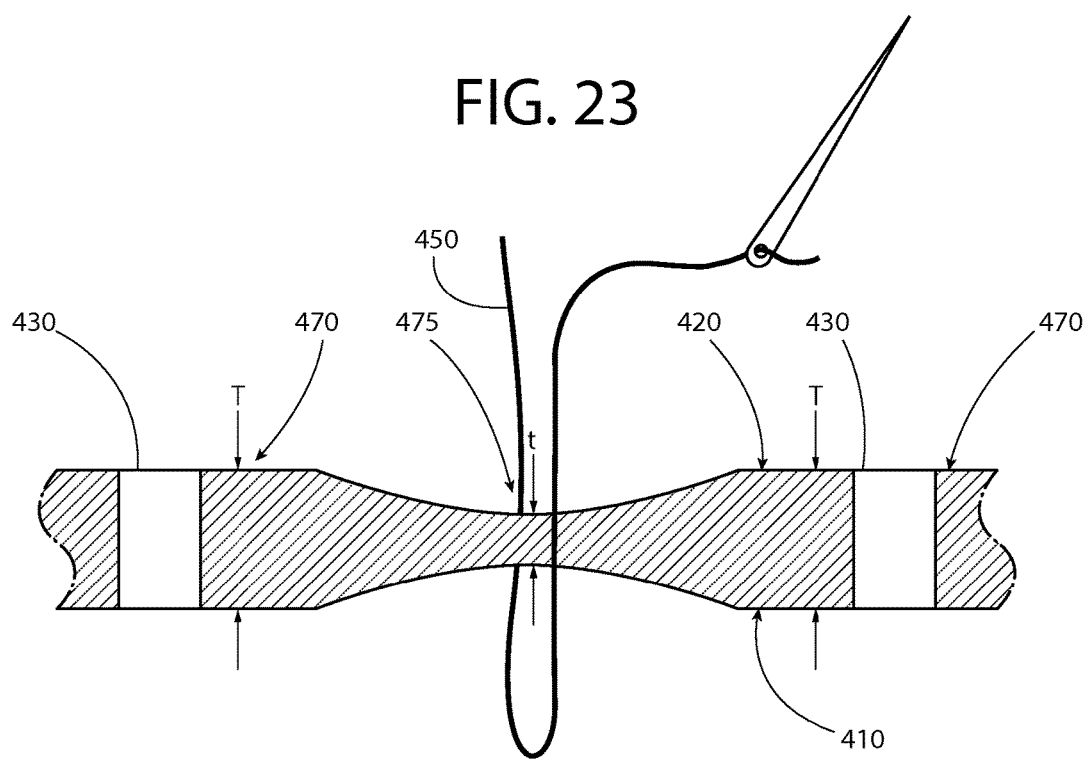
Figure 25:
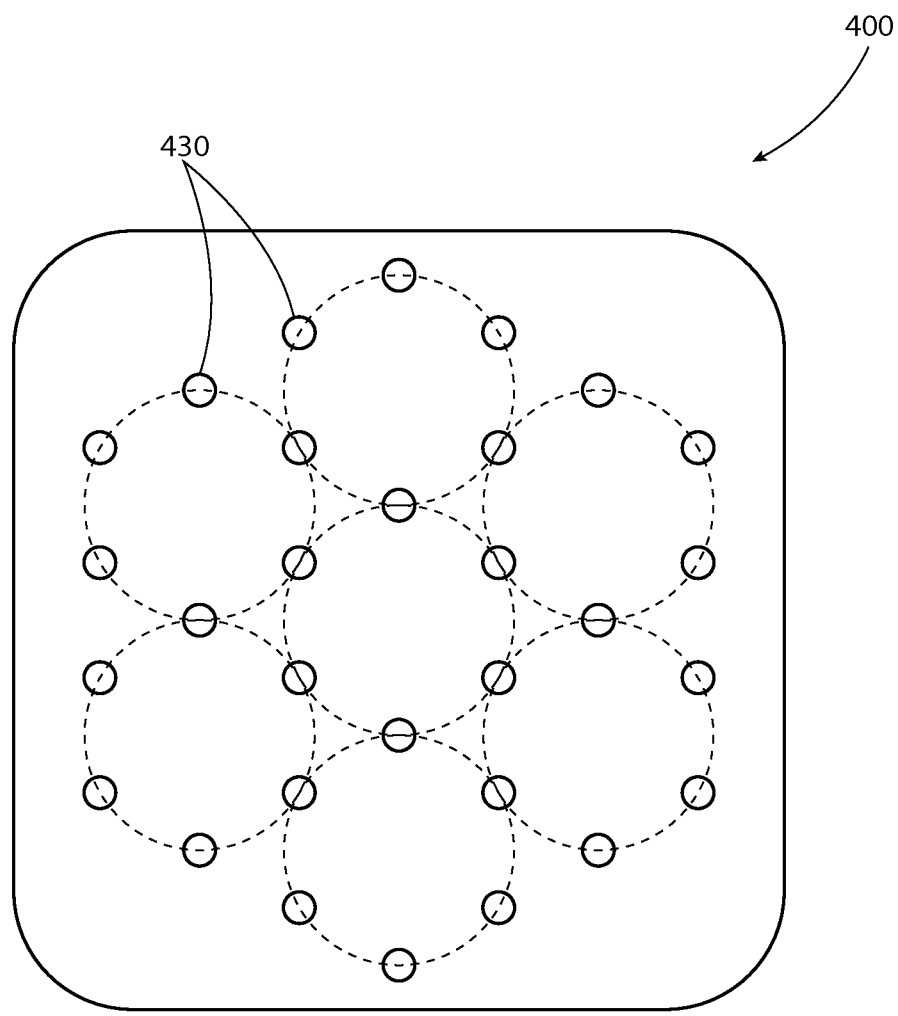
Figure 26:
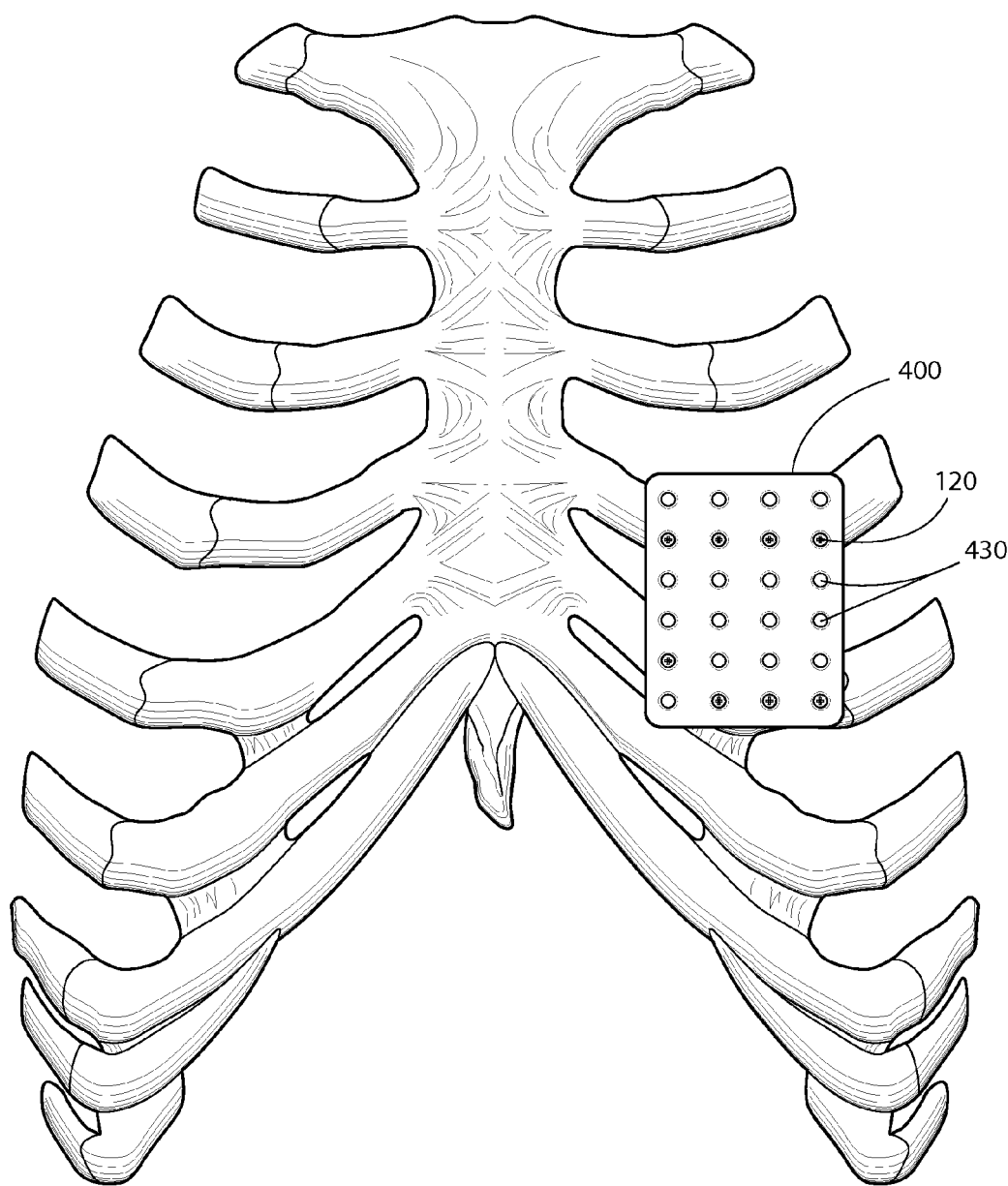

Having thus described the invention in general terms, reference will now be made to the accompanying drawings, which are not necessarily drawn to scale, and wherein:

FIG. 1 shows a schematic representation of a rib cage with bone fixation implants applied to portions of a dissected sternum;

FIG. 2 shows a schematic representation of a rib cage with bone fixation implants applied to a pair of ribs;

FIG. 3 shows a schematic representation of a jaw with a bone fixation implant applied to portions of the jaw bone;

FIG. 4 shows a top view of a bone fixation implant having a wire structural portion in accordance with an exemplary embodiment of the present invention;

FIG. 4A shows a first cross-section of the bone fixation implant of FIG. 4 in accordance with an exemplary embodiment of the present invention;

FIG. 4B shows a second cross-section of the bone fixation implant of FIG. 4 in accordance with an exemplary embodiment of the present invention;

FIG. 4C shows the cross-section of FIG. 4B with a fastener in accordance with an exemplary embodiment of the present invention;

FIG. 5 shows a top view of a bone fixation implant having a plate structural portion in accordance with an exemplary embodiment of the present invention;

FIG. 5A shows a first cross-section of the bone fixation implant of FIG. 5 in accordance with an exemplary embodiment of the present invention;

FIG. 5B shows a second cross-section of the bone fixation implant of FIG. 5 in accordance with an exemplary embodiment of the present invention;

FIG. 6 shows a bone fixation implant having a single wire structural portion in accordance with an exemplary embodiment of the present invention;

FIG. 6A shows a bone fixation implant having an undulating single wire structural portion in accordance with an exemplary embodiment of the present invention;

FIG. 7 shows a bone fixation implant having a dual wire structural portion in accordance with an exemplary embodiment of the present invention;

FIG. 7A shows a bone fixation implant having an undulating dual wire structural portion in accordance with an exemplary embodiment of the present invention;

FIG. 8 shows a bone fixation implant configured for attachment to a patient's sternum in accordance with an exemplary embodiment of the present invention;

FIG. 9 shows a close-up view of the bone fixation implant of FIG. 8 showing a textured engaging surface in accordance with an exemplary embodiment of the present invention;

FIG. 10 shows a bone fixation implant having a textured bone contacting surface in accordance with an exemplary embodiment of the present invention;

FIG. 11 shows a bone fixation implant configured for attachment to a patient's ribs in accordance with an exemplary embodiment of the present invention;

FIG. 12 shows a bone fixation implant configured for attachment to a patient's facial bones in accordance with an exemplary embodiment of the present invention;

FIG. 13 shows a bone fixation implant having a wire mesh structural portion in accordance with an exemplary embodiment of the present invention;

FIG. 14 shows a bone fixation implant having a wire mesh structural portion in accordance with another exemplary embodiment of the present invention;

FIG. 15 shows a telescoping bone fixation implant for a spinal procedure having a cylindrical structural portion in accordance with another exemplary embodiment of the present invention;

FIG. 16 shows an expandable bone fixation implant for a spinal procedure having a coil wire structural portion in accordance with another exemplary embodiment of the present invention;

FIG. 17 shows bone fixation implants for a longitudinal sternal closure procedure in accordance with another exemplary embodiment of the present invention;

FIG. 18 shows a bone fixation implant for a rib approximation procedure in accordance with another exemplary embodiment of the present invention;

FIG. 19 shows a bone fixation implant including enclosed channels according to another example embodiment of the present invention;

FIG. 20 shows a schematic side view of one of the enclosed channels shown in FIG. 19 eyelets an example embodiment of the present invention;

FIG. 21 shows a bone fixation implant including eyelets according to another example embodiment of the present invention;

FIG. 22 shows a schematic side view of one of the eyelets shown in FIG. 21 eyelets according to an example embodiment of the present invention;

FIG. 23 shows a bone fixation implant including a textured tissue-engaging surface according to another example embodiment of the present invention;

FIG. 24 shows a schematic cross-sectional view of a region of reduced thickness according to another example embodiment of the present invention;

FIG. 25 shows a bone fixation implant having a circular lattice structure according to another example embodiment of the present invention; and FIG. 26 illustrates attachment of a bone fixation implant according to FIGS. 19-25 to a patient's ribs for reconstruction of a chest wall prior to attachment of the bone fixation implant to overlying tissue structure (not shown for simplicity) according to another example embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "lateral" and "laterally" refer to a location of an anatomical structure (such as a bone) or movement in a direction towards a point that is farthest from the center of the respective structure. Similarly, the terms "medial" and "medially" refer to a location or movement towards a point closest to the center of the respective structure. The terms "upper" and "lower" are used for explanatory purposes in the examples provided below, where the term "upper" indicates a position or structure that is located toward the head of a human patient with respect to another structure and the term "lower" indicates a position or structure that is located toward the feet of a human patient wither respect to another structure. Furthermore, although each example described herein refers to devices, systems, and methods for supporting ribs, sternum portions, facial bones, and/or spinal bones, embodiments of the described invention may be used to hold together and/or approximate other bones, as well.

Referring now to FIGS. 1-3, different situations are shown in which bone fixation implants may be used to support fractured or broken bones. In FIG. 1, for example, sternal plates 10 may be used to support two portions of a patient's sternum 15 following a sternotomy. In the depicted scenario, two plates 10 are attached to two portions of the dissected sternum 15, respectively, using fasteners 20, such as bone screws. Wires 25 may then wrapped around the plates to hold the two sternum portions together while the sternum heals.

In FIG. 2, rib plates 30 are used to approximate a pair of ribs 35. In this case, the plates 30 are attached, e.g., using fasteners 40, to an adjacent pair of fractured ribs 35, spanning a fracture 45. In addition, wires 50 may be used to support the ribs 35 with respect to each other, thereby approximating the ribs.

In FIG. 3, a facial plate 60 is used to support two portions of a patient's jaw 65 following jaw surgery. In this case, the plate 60 is attached to each portion of the jaw bone 65, spanning the cut 70 that was made by the surgeon during surgery. The plate 60 may be attached to the bone using fasteners 75.

As described in the three scenarios shown in FIGS. 1-3, often a bone fixation plate must come into contact with other implants, such as wires and fasteners, to provide proper support at the target site. In some cases, the plates, wires, and/or fasteners may be made of different metals. The plate may, for example, be made of titanium; the screws may be made of stainless steel; and the wires may be made of stainless steel or aluminum. Direct contact between dissimilar metals, for example in the presence of bodily fluids, may in some cases present a risk of corrosion of one or more of the implants. Corrosion within the body, especially at the site of an injury, could lead to serious complications, at best resulting in pain or discomfort to the patient and at worst resulting in more severe injury and possibly requiring further surgery to correct.

Accordingly, embodiments of the present invention provide a bone fixation implant that is configured to be attached to one or more portions of bone, in which a polymer material covers a metal part of the implant so as to prevent direct contact of the metal of the implant with the metal of other parts of the system, such as the metal of the fasteners and/or of the wires that engage the implant. In particular, and with reference to FIGS. 4-4B, embodiments of the bone fixation implant 100 may comprise at least one structural portion 105 comprising metal and a polymer body 110 at least partially surrounding the at least one structural portion. The polymer body 110 may define an overall shape of the bone fixation implant, corresponding to the outer edge 101 of the bone fixation implant 100, which may include an overall width w, an overall length 1, and an overall thickness t. The polymer body 110 may be configured to receive an attachment member (e.g., fastener 120 shown in FIG. 4C) therethrough for attaching the bone fixation implant 100 to the underlying bone, as discussed in greater detail below. The polymer body 110 may further define an engaging surface 115 that is configured to engage the attachment member as shown in FIG. 4C, such that direct contact between the metal of the structural portion 105 and the attachment member is prevented, as described below.

The structural portion 105 may comprise, for example, at least one metal such as titanium, aluminum, stainless steel, or other biocompatible metal. The polymer body 110 may comprise any polymer material, including, for example, shape memory polymers, polyether ether ketone (PEEK), or other thermoplastic polymers. In some embodiments, the polymer material may be treated or impregnated with an additive. For example, the polymer material may be impregnated with medication, antibiotics, growth factors, bone stimulators, etc. Depending on the particular configuration of the structural portion 105, as described in greater detail below, the structural portion may be formed separately from the polymer body 110 and then embedded into or coated with the polymer material of the polymer body to form the bone fixation implant 100. In other embodiments, however, the polymer body 110 may be formed first and may include grooves or channels into which the metal material of the structural portion may be injected to form the bone fixation implant 100.

In some cases, the structural portion 105 may comprise one or more wires 107, as shown in FIGS. 4, 4A, and 4B. For example, the structural portion 105 may include at least one of a flat wire or a round wire having a diameter of approximately 0.5 mm to approximately 3 mm. In other cases, however, the structural portion 105 may comprise a metal plate 125, as shown in FIGS. 5, 5A, and 5B, and the polymer body 110 may comprise a coating or covering that at least partially surrounds the metal plate, such as to at least cover areas of the plate that are configured to come into contact with the metal components of the implant system (e.g., wires and/or fasteners, as described in greater detail below). In still other cases, the structural portion 105 may be a mesh of wires that are embedded in the polymer body, as shown in FIGS. 13 and 14 and described below.

In some embodiments, the polymer body 110 completely surrounds the metal forming the structural portion 105 (e.g., completely surrounding the wires 107 as shown in FIG. 4, the plate 125 as shown in FIG. 5, or the mesh 170 as shown in FIGS. 13 and 14). In other embodiments, however, a portion of the structural portion 105 may extend out from the polymer body 110. For example, one end of the bone fixation implant may be configured such that the metal of the structural portion 105 is exposed, and the exposed portion may be configured to allow or facilitate a surgeon's removal of part of the exposed portion. In some cases in which the structural portion is a metal plate, for example, the exposed portion may include notches or lines of weakness along which a surgeon may be able to break off part of the structural portion, such as to trim an overall length of the bone fixation implant.

Turning again to FIGS. 4-5B, 13, and 14, the polymer body 110 may define one or more openings 140 that are configured to receive the attachment member (e.g., the fastener 120 of FIG. 4C) therethrough. For example, the structural portion 105 may define an inner polymeric region 116 of the polymer body 110 on one side of the structural portion 105 and an outer polymeric region 119 of the polymer body 110 on an opposite side of the structural portion. The inner polymeric region 116 may define the opening 140, and the engaging surface 115 may be defined around a circumference of the opening, as shown. In this way, the polymer material in the inner polymeric region 116 may be disposed between the metal material of the attachment member passed through the opening 140 and the metal material of the structural portion 105, such that, for example, a fastener 120 received by the opening does not come into contact with the structural portion in the vicinity of the opening, but rather only engages the polymer body 110.

The opening 140 (defined by the engaging surface 115 of the polymer body 110) may, in some embodiments, have a diameter that is at least slightly smaller (e.g., approximately 0.5% to 15% smaller) than a diameter of the attachment member (e.g., fastener 120) to be received therethrough, as shown in FIG. 4C. In other cases, however, such as in the example depicted in FIG. 5, the opening may be a puncture that is made through a solid piece of the polymer body 110, such that the puncture defines the engaging surface 115. In this way, more of the polymer body 110 may be available for engagement with the fastener 120 as the fastener is inserted through the material of the inner polymeric region 116 via the puncture, allowing for more secure attachment of the fastener with the bone fixation implant and the underlying bone.

Moreover, in such cases as shown in FIGS. 4-4C and 5-5B, the engaging surface 115 may be configured to form a seal around at least a portion of the attachment member passing therethrough. Thus, as the attachment member (e.g., the fastener 120, which may be a bone screw or self-locking screw) bites through the material of the polymer body 110 in the inner polymeric region 116 and advances into the bone fixation implant 100 and the underlying bone, the engaging surface 115 of the polymer body may tightly engage and form a seal around the threads of the attachment member (e.g., the fastener 120), thereby minimizing the amount of fluid (e.g., blood and other bodily fluids) that may pass through the puncture or opening 140 from one side of the bone fixation implant 100 to the other.

With reference now to FIGS. 4-7, the structural portion 105 may have various configurations (e.g., shapes and sizes) to accommodate different types of bone fixation implants for use in different parts of the body. For example, in FIGS. 4-4B, the structural portion 105 comprises a wire 107 that is shaped to correspond to the overall shape of the implant 100. Thus, in FIGS. 4-4B, the wire 107 (e.g., when considered apart from/not covered by the polymer body 110) defines receiving portions 130 and connecting portions 145 extending between adjacent receiving portions. At least a portion of the structural portion 105 (e.g., the connecting portions 145) may be substantially aligned with a central axis A of the bone fixation implant 100. The polymer body 110, in this case, may define the overall shape of the implant 100, including the contours of the perimetral edge 101 of the bone fixation implant and the thickness t of the implant (shown in FIGS. 4A and 4B).

In other embodiments, such as those shown in FIGS. 6 and 7, at least a portion of the structural portion 105 may be substantially aligned with an edge of the bone fixation implant 100. In FIG. 6, for example, the structural portion comprises a single wire 107 that extends along and is substantially aligned with a first edge 152 of the bone fixation implant 100. The second edge 154 opposite the first edge 152 may be defined solely by the polymer body 110. In the depicted example of FIG. 6, the bone fixation implant 100 may be disposed within the patient's body such that the reinforced first edge 152 is positioned to withstand any additional forces that may be imparted on that side of the implant, as described in greater detail below.

In some cases, as shown in FIG. 7, the structural portion 105 may comprise a first wire 107a that extends along and is substantially aligned with the first edge 152 of the bone fixation implant 100 and a second wire 107b that extends along and is substantially aligned with the second edge 154 of the bone fixation implant. In some embodiments, the first wire 107a may be longer, thicker, and/or made of a different material than the second wire 107b. The particular configuration of each wire 107a, 107b may be selected based on where in the body and how the bone fixation implant 100 is to be installed. In this way, the first edge 152, which may have greater reinforcement in the form of a longer and/or thicker wire and/or a wire made of a stronger material, may be disposed in a position in the patient's body so as to absorb a greater amount of force or stress as compared to the second edge 154, which may have less reinforcement.

Furthermore, in some cases, the wires 107, 107a, and 107b, although following a path that is substantially aligned with the first edge 152 of the respective bone fixation implants 100, may have an undulating curved shape, as shown in FIGS. 6A and 7A. Thus, rather than maintaining the same distance from a respective edge 152, 154 or surface (e.g., bone contacting surface 160 shown in FIG. 10 and described below) of the bone fixation implant along the length of the wire 107, 107a, 107b, as shown in FIGS. 6 and 7, the undulations in the wires shown in FIGS. 6A and 6B may instead cause the wire to be disposed closer or farther away from the respective edge 152, 154 or surface depending on where along the length of the wire the distance is measured. Such undulations may, for example, impart greater pliability to the bone fixation implant 100 so as to allow a surgeon to shape the implant to correspond to the shape or surface contour of the bone to which the implant is to be fixed.

Moreover, in some embodiments, in addition to variations in the configuration (e.g., size, shape, material, etc.) of the structural portion 105, the configuration of the polymer body 110 may also vary depending on the intended use of the bone fixation implant 100. Turning to FIG. 8, for example, a bone fixation implant 100 is shown that is configured for use in longitudinal sternal fixation (e.g., for closure of a sternal dissection such as shown in FIG. 1). In the depicted example, the bone fixation implant 100 is configured such that the structural portion 105 comprises a single wire 107 that extends along at least a portion of the first edge 152 of the implant and is substantially aligned with the first edge. The bone fixation implant 100 of FIG. 8 may be installed on one portion of a patient's sternum 15, as illustrated in FIG. 1, with another similarly configured (e.g., a mirror image of the bone fixation implant 100 shown in FIG. 8) attached to the opposite portion of the dissected sternum. The implants 100 may be oriented such that the reinforced, first edge 152 of each implant is disposed along a lateral edge 17 of the sternum (FIG. 1).

Accordingly, in some embodiments, a first attachment member (e.g., the fastener 120 shown in FIG. 4C) may be used to attach the bone fixation implant to the underlying bone via the openings 140 in the polymer body 110, and the polymer body may be further configured to receive a second attachment member (e.g., a wire 25 shown in FIG. 1) that is configured to be wrapped around the bone fixation implants 100 and a corresponding portion of the underlying bone to hold the sternum portions 15 together, as shown in FIG. 1. As shown, the reinforced first edge 152 of each implant 100 (FIG. 8) may be positioned such that the wire 107 of the structural portion 105 supports the wire 25 of the second attachment member. In this case, the engaging surface defined by the polymer body 110 may be defined on an edge of the bone fixation implant (e.g., the first edge 152) and may be configured to engage the second attachment member (e.g., the wire 25), such that although the wire 107 forming the structural portion supports the attachment member wire 25, the attachment member wire is prevented from coming into direct contact with the structural portion due to the intervening material of the polymer body.

To facilitate the engagement of a second attachment member such as a wire 25, as in the scenarios depicted in FIG. 1 for a longitudinal sternal closure and in FIG. 2 for a rib approximation procedure, in some embodiments the engaging surface 115 of the polymer body 110 may define a texture that is configured to enhance engagement of the bone fixation implant 100 with the attachment member, as shown in FIG. 9. For example, the engaging surface 115 may include knurls 117, bumps, protrusions, or other texturing features that help the polymer body 110 grip the attachment member (e.g., the wire 25 of FIG. 1 or the wire 45 of FIG. 2) in the region of the first edge 152 of the implant 100.

As shown in FIG. 10, in still other embodiments, the polymer body 110 may further define a bone contacting surface 160, and the bone contacting surface may define a texture (e.g., knurls 117, bumps, protrusions, or other texturing features) that is configured to enhance engagement of the bone fixation implant with the bone on which the implant is placed for installation. The texturing of the bone contacting surface 160 may, for example, increase the frictional engagement between the bone fixation implant 100 and the surface of the bone on which the implant is to be installed, such that the implant has less of a tendency to move with respect to the bone during the installation process (e.g., while fasteners, such as bone screws, are being screwed into the implant and underlying bone). This increased frictional engagement may enhance the stability of the bone fixation implant with respect to bone, such that installation of the implant can be simplified and the accuracy of the placement can be improved. In addition, the textured surface may promote the creation of scar tissue by the patient's body, further enhancing fixation of the implant following the procedure as the body heals.

As noted above, the bone fixation implant 100 can be configured in many ways to accommodate installation in various parts of a patient's body. The bone fixation implant 100 shown in FIG. 8, for example, is configured to be attached to a patient's sternum (e.g., similar to what is shown in FIG. 1), whereas the bone fixation implant 100 shown in FIG. 11 is configured to be attached to a patient's ribs. In another scenario, the bone fixation implant may be configured to be attached to a patient's facial bone, such as the bone fixation implant 100 shown in FIG. 12.

In still other embodiments, the structural portion 105 may comprise a wire mesh, as shown in FIGS. 13 and 14, and the polymer body 110 may surround the structural portion to create a sheet-like bone fixation implant 100 that can be used for repair of a defect in a patient's chest wall (e.g., when a tumor is removed), for pelvic reconstruction, and/or for reconstruction of the skull. The configuration of the wire mesh forming the structural portion 105 may vary to accommodate different applications. In FIG. 13, for example, the wire mesh of the structural portion 105 includes undulations (as described above with respect to FIGS. 6A and 7A), whereas in FIG. 14 the wire mesh of the structural portion is a straight-line grid. Moreover, although the angles formed by the grid in FIG. 14 are approximately 90°, in other embodiments a straight-line grid may be used that forms angles between the wires of the mesh that are greater than or less than approximately 90°. The overall shape (e.g., surface area) of the mesh embodiment of the bone fixation implant 100 shown in FIGS. 13 and 14 may be adjustable by the surgeon in some cases in which the surgeon is able to cut or remove portions of the implant (e.g., portions of the polymer body 110 and/or the structural portion 105) to achieve a desired shape. In this way, bone fixation implants 100 may be formed having different sizes and shapes of grids to accommodate numerous different procedures in various locations within the patient's body.

In this regard, and with reference to FIGS. 19-26, a bone fixation implant 400 may thus be provided that has a bone engaging surface 410 and a tissue-engaging surface 420 opposite the bone-engaging surface. The bone fixation implant 400 may define a plurality of openings 430 that are arranged across an overall length L and an overall width W of the bone fixation implant, and each opening 430 may extend through the bone-engaging surface 410 and the tissue-engaging surface 420. Each opening 430 may be configured to receive an attachment member (e.g., fastener 120 shown in FIG. 4C) for securing the bone fixation implant to an underlying bone structure (e.g., flail ribs or other bone structure to be treated) such that the bone-engaging surface of the bone fixation implant engages (e.g., contacts) the underlying bone structure. Moreover, the bone fixation implant may be configured to be secured to an overlying tissue structure (e.g., soft tissue and/or muscle) such that the tissue-engaging surface 420 of the bone fixation implant engages (e.g., contacts) the overlying tissue structure, thereby encouraging incorporation of the tissue structure into the bone fixation implant to promote stabilization of the region, including the underlying bone structure, during healing.

By engaging the overlying tissue structure with the bone fixation implant, it is believed that the bone will heal faster. For example, although it may take weeks or even months for bone to heal, it may take only a few days or a week or two for muscle and/or soft tissue to incorporate with the bone fixation implant. With respect to fixation of ribs, for example, engagement of the overlying tissue structure with the bone fixation implant 400 may serve to create a new chest wall, which should reduce the pain experienced by the patient during movement or breathing while the ribs heal. Even if the underlying bone (e.g., the ribs) do not fully heal, the bone fixation implant 400 as shown in FIGS. 19-26, when used as described herein, is designed replicate the patient's chest wall. Accordingly, embodiments of the bone fixation implant 400 may be used in the treatment of flail ribs and pectus pathology, as well as in other locations as described above (e.g., the skull/scalp).

With respect to chest wall reconstruction, for example, the material of the bone fixation implant may be selected to match the range of motion and pliability of the chest wall, which may vary depending on the area of the chest wall being treated. For example, some embodiments of the bone fixation implant may include a structural portion 105 made of titanium, aluminum, stainless steel, Nitinol, or some other metal (e.g., in the form of a wire, a plate, or a mesh, as described above with respect to FIGS. 13 and 14) and may also include a polymer body, which may be made of PEEK. In other embodiments, however, such as in applications in which greater pliability is required, the bone fixation implant 400 may be made predominantly or solely of a polymer, such as PEEK. Conversely, where greater rigidity (less pliability) is required for the particular application, the bone fixation implant 400 may be made predominantly or solely of metal, such as titanium, aluminum, stainless steel, Nitinol, or other biocompatible metal.

The bone fixation implant 400 may be configured to be secured to overlying tissue structure (e.g., via sutures) in various ways. In some embodiments, shown in FIGS. 19 and 20, for example, the tissue-engaging surface 420 may comprise a plurality of enclosed channels 440 extending substantially parallel to the bone fixation implant 400. Each enclosed channel 440 may define a first open end 442 and a second open end 444, and a lumen 446 may be provided between the two ends such that the enclosed channel 440 is configured (e.g., sized with an appropriate length, diameter, and shape) to receive a suturing needle therethrough via the first and second open ends. Thus, as shown in FIG. 20, a suturing needle may apply a suture stitch through the overlying tissue, then be passed through the enclosed channel 440, thereby threading a suture thread 450 (resorbable or permanent) through the enclosed channel. By selecting one or more of the enclosed channels 440 to receive the suture thread 450, the overlying tissue structure can be secured to the bone fixation implant using sutures that extend from the tissue structure through the selected enclosed channels. Accordingly, a number of enclosed channels 440 may be provided, as shown in FIG. 19, and they may be arranged at different angles with respect to one another as shown so as to provide the surgeon with the ability to select one or more enclosed channels based on their location and/or their orientation to match the particular application and surgeon's methods and preferences for the given procedure.

In other embodiments, securement to the overlying tissue may be accomplished via eyelets 460, as shown in FIGS. 21 and 22. The bone fixation implant 400 may, for example, include a plurality of eyelets 460 extending outwardly from the tissue-engaging surface 420, where each eyelet is configured (e.g., sized and shaped) to receive a suturing needle therethrough. In this way, the overlying tissue structure may be securable to the bone fixation implant 400 using sutures 450 that extend from the tissue structure through at least one of the eyelets 460, as shown in FIG. 22.

As noted above with respect to FIGS. 13 and 14, in some cases the bone fixation implant may comprise at least one structural portion 105 comprising metal and a polymer body 110 (e.g., made of PEEK) at least partially surrounding the at least one structural portion. The polymer body 110 may define the overall shape of the bone fixation implant, where the shape includes the overall width W, the overall length L, and the overall thickness T (shown, e.g., in FIGS. 19 and 21). The polymer body 110 may define the openings 430, such that direct contact between the metal of the structural portion 105 and the attachment member (e.g., the fastener) is prevented.

In some cases, for example, the polymer body 110 may define the bone-engaging surface 410, the tissue-engaging surface 420, and the enclosed channels 440 such that direct contact between the metal of the structural portion and any of the bone structure, the tissue structure, or the sutures is prevented. The enclosed channels 440 may, for example, be integrally formed with the polymer body 110. In still other cases, the polymer body 110 may define the bone-engaging surface 410, the tissue-engaging surface 420, and at least a portion of the eyelets 460 (e.g., via a coating or covering of the eyelets) such that direct contact between the metal of the structural portion and any of the bone structure, the tissue structure, or the sutures is prevented.

In some embodiments, rather than having enclosed channels or eyelets, the bone fixation implant itself is configured to allow a suturing needle to be passed through the material of the implant in certain regions to secure the overlying tissue to the implant. Turning to FIGS. 23 and 24, for example, an overall thickness T of the bone fixation implant at a rim 470 of each opening 430 may be greater than the overall thickness t in a region 475 between adjacent openings. Thus, the region 475 between adjacent openings 430 may be configured to receive a suturing needle therethrough (e.g., due to its reduced thickness), such that the overlying tissue structure is securable to the bone fixation implant using sutures extending from the tissue structure through the region. In this regard, the spacing of the openings 430, the pattern of the arrangement of openings 430, and/or the material(s) of the bone fixation implant (e.g., in the region 475) may be selected to allow a suture needle to be inserted through the tissue-engaging surface 420 of the implant and out the bone-engaging surface 410, reversed in direction, inserted through the bone-engaging surface 410 and out through the tissue-engaging surface 420, thereby completing a single suture stitch through the bone fixation implant 400.

Accordingly, the arrangement of the openings 430 may vary based on the particular application (e.g., the part of the body to be treated, etc.) to provide sufficient spacing to allow the suture needle to maneuver and interact with the bone fixation implant as needed. Thus, although a rectangular lattice structure is shown in the embodiments depicted in FIGS. 19, 21, and 23, the openings 430 may be arranged to form nodes of a variety of different lattice structures, based on the particular application and/or the surgeon's preferences. For example, a circular lattice structure is shown in FIG. 25, and any of a number of other different lattice structures (e.g., triangular, pentagonal, hexagonal, etc.) may be used.

With reference to FIG. 23, in some embodiments, at least one of the bone-engaging surface 410 or the tissue-engaging surface 420 (and in some cases, both surfaces) may define a texture 480 that is configured to enhance engagement of the bone fixation implant with the underlying bone structure of the overlying tissue structure, respectively. The texture 480 may, for example, be a roughening of the surface, such as may be caused by knurls, one or more score lines, protrusions, etc. formed in the respective surface. In some cases, the enclosed channels 440 and eyelets 460 may create enough of a texturing effect so as to promote incorporation of the overlying tissue structure with the bone fixation implant, in which case no additional surface texturing may be required.

Accordingly, a method of fixating bone is provided. With respect to the repair of the chest wall of a patient, for example, the surgeon may initially separate the muscle and/or soft tissue from the chest wall. Fluoroscopy may be used to allow the surgeon to see where the worst fractures are, such that the surgeon can choose an appropriate location for the incision and identify appropriate areas of the bone structure for attachment of the bone fixation implant.

An appropriate bone fixation implant (e.g., appropriate size and materials of construction) may be selected by the surgeon, and the bone fixation implant may be applied to at least one portion of bone, where the bone fixation implant has a bone-engaging surface and a tissue-engaging surface opposite the bone-engaging surface, as described above. The bone fixation implant may define a plurality of openings arranged across an overall length and an overall width of the bone fixation implant, and the openings may extend through the bone-engaging surface and the tissue-engaging surface. In some cases, the overall shape of the bone fixation implant may be modified (e.g., adjusted) by cutting off a portion of the bone fixation implant to correspond to a shape of an area of the underlying bone structure to be treated.

The bone fixation implant may then be secured to the underlying bone structure (e.g., the ribs), such as by inserting an attachment member (e.g., a fastener, such as a self-locking screw) into a respective one of the openings. In this way, the bone-engaging surface of the bone fixation implant may engage the underlying bone structure. In some cases, the insertion of the attachment members through the openings may be monitored by the surgeon in real time using a thoracoscopic camera to ensure that an attachment member having the correct length has been selected.

Once the bone fixation implant has been secured to the underlying bone structure (e.g., as shown in FIG. 26), the overlying tissue structure may be sutured to the bone fixation implant such that the tissue-engaging surface of the bone fixation implant engages the overlying tissue structure. For example, a number of sutures may be passed through the overlying tissue structure and the bone fixation implant (e.g., via enclosed channels, eyelets, or regions of reduced thickness), as described above. The sutures may then be cinched by the surgeon (e.g., by applying tension on the suture thread) to bring the overlying tissue structure, which was previously separated from the bone structure, into engagement with the bone fixation implant that is now attached to the bone structure. In this way, incorporation of the tissue structure into the bone fixation implant may be encouraged and facilitated, which may in turn promote stabilization of the underlying bone structure during healing.

In still other embodiments, embodiments of the bone fixation implant 100 may comprise spacers configured for use in spinal reconstruction procedures, such as expandable spacers that can be inserted in a void in spinal bones to support the spine. Such voids may, for example, be the result of a cutting away of tumors in the spine. Examples of bone fixation implants 100 configured as expandable spacers are shown in FIGS. 15 and 16. In FIG. 15, for example, the bone fixation implant 100 comprises a first portion 103 and a second portion 104 configured to be received within and expand outwardly from the first portion. Each of the first and second portions 103, 104 may comprise a structural portion 105 comprising metal and a polymer body 110 comprising a polymeric material such as PEEK, as described above.

In the depicted example of FIG. 15, the polymer body 110 of each portion 103, 104 may be configured in a cup shape, and attachment members (e.g., fasteners 120) may be provided through the upper and lower surfaces 113, 114 of the respective portions that are configured to attach the bone fixation implants to the bones of the spine in the target location. The structural portion 105 provided in each of the first and second portions 103, 104 may be configured as cylinders, such that the cylinders are able to provide support to the bone fixation implant 100 in the direction of expansion, while allowing the metal of the attachment members to engage only the polymer material of the polymer body 110. Due to the telescoping nature of the first and second portions 103, 104, the bone fixation implant 100 may be moved to a contracted position for insertion into the void in the spinal bone through application of force on the upper and lower surfaces 113, 114 by the surgeon, then moved to an expanded position to contact corresponding bone portions within the void when the force is removed. The bone fixation implant 100 may have a bias toward the expanded position, for example, as a result of a spring mechanism or other feature (not shown) configured to bias the first and second portions 103, 104 away from each other. Once in the proper location and in the expanded position within the void, the attachment members (e.g., the fasteners 120) may then be used to secure the bone fixation implant 100 within the spinal bone void.

In the embodiment shown in FIG. 16, the bone fixation implant 100 comprises a single polymer body 110, with an embedded structural portion 105 configured in the shape of a coil, as shown. The structural portion 105 in this case may provide some degree of expansion to the bone fixation implant 100, such due to a force applied by the coil structural portion 105 that serves to bias the upper and lower surfaces 113, 114 of the implant 100 away from each other. In this regard, the structural member 105 may be made of a shape memory alloy, such as Nitinol, that is configured to have a predetermined shape within the polymer body 110 under certain conditions (e.g., at a certain temperature). For example, when cooled, the bone fixation implant 100 may achieve a contracted shape that can be positioned within a void in the target spinal bone. As the bone fixation implant 100 acclimates to the body temperature of the patient, however, the shape memory properties of the structural portion 105 may allow the bone fixation implant 100 to achieve an expanded shape for more fully engaging and supporting the bone within the void (e.g., through contact of the upper and lower portions 113, 114 with corresponding bone surfaces and/or via the user of attachment members as shown in FIG. 15).

As described above and shown in the depicted embodiments of FIGS. 4-16, embodiments of the bone fixation implant described above are configured to create plating systems that can be used to address defects and issues in various locations within a patient's body. Depending on the particular configuration of the bone fixation implant 100 (e.g., the overall shape of the implant, the use of a wire structural portion versus a plate or grid structural portion, the use of a dual wire structural portion versus a single wire structural portion, the use of openings within the polymer body to receive fasteners versus punctures, etc.), the bone fixation implant may be used with attachment members in the form of fasteners and/or in the form of wires that are wrapped around the implant and/or the underlying bone to which the implant is attached. The bone fixation implants 100 may be used in cranio- and maxillofacial surgery; ortho and back surgery; chest wall reconstruction; pelvic reconstruction; etc. Examples of medical devices that may benefit from embodiments of the present invention may include devices described in U.S. Patent Pub. No. 2013/0178906 titled Method and System for Longitudinal Closure of Dissected Sternums, filed on Nov. 16, 2012; U.S. Patent Pub. No. 2013/0338719 titled Method and System for Longitudinal Closure of Dissected Sternums, filed on Aug. 16, 2013; and U.S. Provisional Patent Appl. No. 61/893,420 titled Device System and Method for Supporting and Approximating Ribs, filed on Oct. 21, 2013, the contents of each of which are incorporated by reference herein.

Turning to FIG. 17, for example, in an application in which bone fixation implants 100 including structural portions 105 (not shown) and polymer bodies 110 are provided for closure of a dissected sternum, first and second bone fixation implants 100, 102 may be provided that include at least one extended region 300 and at least one connecting portion 310, where the extended region includes a lateral edge 320 extending away from a midline M of the respective bone fixation implant. Each extended region 300 may be configured to receive at least one second attachment member (e.g., a wire 25 shown in FIG. 1).

In some cases, for example, the extended region 300 may be an arched region, as depicted in FIG. 17. The lateral edge 320 may, in such cases, be rounded, as shown. Although in some embodiments in which the lateral edge 320 is rounded the inner edge 322 of the extended region 300 may also be a rounded edge, as illustrated, in other embodiments the inner edge may not be rounded and may, instead, extend in a linear fashion between either end of the extended region. Furthermore, although the extended regions 300 are depicted in the figures as arched regions having a rounded outer edge 320 (e.g., in the form of an arch), in some embodiments the extended regions may extend away from the midline M in an angular fashion, so as to have a square, rectangular, or trapezoidal profile, for example. Additionally or alternatively, the connecting portions 310, in some embodiments, may be configured to have a somewhat curved edge, such that the connecting portions may themselves have one or more arched regions that are smaller and/or more linear (less curvature and/or degree of lateral extension) as compared to the arches of the extended regions 300 that may be configured to extend past the lateral edges of the sternum portions. The bone fixation implants 100, 102 may define openings 140 as described above that are configured to receive first attachment members (e.g., fasteners 120 shown in FIG. 4C) for fixing the implants to the bone, as described above.

In some cases, the extended regions 300 may comprise at least one groove 330 configured to receive a portion of the second attachment member (e.g., the wire 25) therein. In the depicted embodiment, three grooves 330 are provided in each extended region 300, and each groove extends between the inner edge 322 and the lateral edge 320 of the extended region. In other embodiments, however, fewer or more grooves may be provided. In addition, the groove 330 may only be provided proximate the lateral edge 320. Moreover, the lateral edge 320 may be beveled (e.g., have a gradually reduced thickness as compared to the inner edge 322) to further facilitate receipt of the second attachment member 130 and provide for a lower profile of the system.

Furthermore, in some embodiments, a distal end of the bone fixation implants 100, 102 shown in FIG. 17 may define one or more lines of weakness 165 configured such that the surgeon may cut or break the material of the reinforcing member along the pre-defined line of weakness. The line of weakness 165 may, for example, be formed mechanically, such as via etchings, grooves, or perforations defined in the structural portion (not shown) underlying the polymer body. In still other cases, the polymer body 110 may not cover portions of the structural portion defining the lines of weakness 165, as described above.

As yet another example, in FIG. 18, another embodiment of a bone fixation implant 100 that is configured for approximating a pair of ribs is shown. Similar to the embodiment described above with respect to FIG. 17, the bone fixation implant 100 comprises a structural portion (not shown) configured in one of the ways described above (e.g., as a wire, multiple wires, or a plate) and a polymer body 110. As described with respect to FIG. 17, the bone fixation implant 100 may include at least one extended region 300 and at least one connecting portion 310. In some embodiments, an extension 380 may be provided in the vicinity of the extended regions 300 that includes one or more additional holes 140 configured for receiving a first attachment member (e.g., a fastener 120) therethrough. For example, as depicted in FIG. 18, first and second extensions 380 may protrude from the connecting portions 310 on either side of the extended region 300 therebetween towards each other, leaving a gap 385. The gap 385 may allow the surgeon to apply the appropriate degree of angling via the extended region 300, as described above, while at the same time providing additional areas for the bone fixation implant 100 to be secured to the underlying bone.

Furthermore, the extended regions 300 may comprise one or more holes 370 that are configured to receive a portion of the respective second attachment member (e.g., the wire 25) therethrough for aiding in keeping the second attachment members from moving with respect to the bone fixation implants during installation and following installation. For example, three holes 370 may be provided, as shown, and one or more of the holes may be used to secure a second attachment member, as deemed necessary by the surgeon for fixating the ribs. Moreover, in some cases, the holes 370 may be provided in conjunction with the grooves (described above with respect to FIG. 17), such that the surgeon may choose which of the two methods to employ to keep the system in place considering the condition of the patient and other surgical variables and considerations.

In addition to minimizing reactions between different metal components (e.g., the metal in the implant and the metal in the fasteners), the use of a structural portion comprising metal that is at least partially surrounded by a polymer body as described above may also impart a certain degree of malleability and resiliency to the bone fixation implant, which may allow the implant to be molded by a surgeon during surgery to the shape and contour of the patient's native bone or body structure to which the implant is being applied. Moreover, the use of PEEK or other shape memory polymers in the polymer body, where such materials have the ability to return from a (temporary) deformed state to a (permanent) original shape, may serve to relieve some of the stresses experienced by the installed implants that may otherwise be borne solely by the metal components of the bone fixation implant. Furthermore, use of a polymer body as described above may also provide for less metal to be used in the structural portion, thereby allowing bone fixation implants having a thinner profile to be created, which in turn may minimize the pain and discomfort experienced by the patient as the patient heals and resumes daily activities.

A method of fixating bone using one or more bone fixation implants as described above is also provided. A bone fixation implant may be applied to at least one portion of bone, where the bone fixation implant comprises at least one structural portion comprising metal and a polymer body at least partially surrounding the at least one structural portion. The polymer body may define an overall shape of the bone fixation plate comprising an overall width, an overall length, and an overall thickness. A portion of an attachment member may be passed through the polymer body to attach the bone fixation plate to underlying bone, where the polymer body defines an engaging surface configured to engage the attachment member, such that direct contact between the metal of the structural portion and the attachment member is prevented, as described above.

In some cases, the attachment member may be a first attachment member (e.g., a fastener), and a second attachment member (e.g., a wire) may be wrapped around the bone fixation plate and a corresponding portion of the bone. The structural portion may define an inner polymeric region of the polymer body on one side of the structural portion and an outer polymeric region of the polymer body on an opposite side of the structural portion. The inner polymeric region may define at least one opening configured to receive the attachment member therethrough, and the portion of the attachment member may be passed through the opening. In some embodiments, the engaging surface may be defined around a circumference of the at least one opening and may be configured to form a seal around a portion of the attachment member, as described above.

Moreover, as described above, the polymer body may comprise polyether ether ketone (PEEK), and the structural portion may comprise at least one of titanium, aluminum, stainless steel, or Nitinol. In some cases, a portion of the structural portion may extend out from the polymer body, and at least part of the portion of the structural portion extending out from the polymer body may be removed (e.g., broken off or cut by the surgeon) to adjust a length of the bone fixation implant.

Many modifications and other embodiments of the invention will come to mind to one skilled in the art to which this invention pertains having the benefit of the teachings presented in the foregoing descriptions and the associated drawings. For example, although particular configurations (e.g., shapes and sizes) of bone fixation implants are described above and depicted in the figures, numerous other bone fixation implants configured to treat other parts of the patient's body may benefit from embodiments of the present invention. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of fixating bone of a chest wall of a patient, the method comprising:
    separating muscle or soft tissue from the bone of the chest wall;
    applying a bone fixation implant to at least one portion of the bone of the chest wall, wherein the bone fixation implant has a bone-engaging surface and a muscle or soft tissue-engaging surface opposite the bone-engaging surface, wherein the bone fixation implant defines a plurality of openings arranged across an overall length and an overall width of the bone fixation implant and extending through the bone-engaging surface and the muscle or soft tissue-engaging surface,
    inserting an attachment member into a respective one of the openings to secure the bone fixation implant to an underlying bone structure such that the bone-engaging surface of the bone fixation implant engages the underlying bone structure, and
    suturing an overlying muscle or soft tissue structure to the bone fixation implant such that the muscle or soft tissue-engaging surface of the bone fixation implant engages the overlying muscle or soft tissue structure, thereby encouraging incorporation of the muscle or soft tissue structure into the bone fixation implant to promote stabilization of the underlying bone structure during healing.

2. The method of claim 1 further comprising modifying an overall shape of the bone fixation implant by cutting off a portion of the bone fixation implant to correspond to a shape of an area of the underlying bone structure to be treated.

3. The method of claim 1, wherein the muscle or soft tissue-engaging surface comprises a plurality of enclosed channels extending substantially parallel to the bone fixation implant wherein suturing the overlying muscle or soft tissue structure to the bone fixation implant comprises passing a suturing needle through the overlying muscle or soft tissue structure and at least some of the enclosed channels.

4. The method of claim 3, wherein the enclosed channels are arranged at different angles with respect to each other.

5. The method of claim 3, wherein the bone fixation implant further comprises:
    at least one structural portion formed of metal; and
    a polymer body at least partially surrounding the at least one structural portion,
    wherein the polymer body defines an overall shape of the bone fixation implant comprising the overall width, the overall length, and an overall thickness,
    wherein the polymer body defines the openings, such that direct contact between the metal of the structural portion and the attachment member is prevented, and
    wherein the polymer body defines the bone-engaging surface, the muscle or soft tissue-engaging surface, and the enclosed channels such that direct contact between the metal of the structural portion and any of the bone structure, the muscle or soft tissue structure, or sutures is prevented.

6. The method of claim 1, wherein suturing the overlying muscle or soft tissue structure to the bone fixation implant comprises passing a suturing needle through a region of the bone fixation implant between adjacent openings, wherein an overall thickness of the bone fixation implant at a rim of each opening is greater than the overall thickness in the region between adjacent openings.

7. The method of claim 1, wherein inserting the attachment member into the respective one of the openings comprises thorocoscopically monitoring the attachment member as it is inserted.

8. The method of claim 1, wherein the muscle or soft tissue-engaging surface comprises a plurality of eyelets extending outwardly from the muscle or soft tissue-engaging surface, wherein suturing the overlying muscle or soft tissue structure to the bone fixation implant comprises passing a suturing needle through the overlying muscle or soft tissue structure and at least some of the eyelets.

9. The method of claim 8, wherein the eyelets are arranged at different angles with respect to each other.

10. The method of claim 8, wherein the bone fixation implant comprises:
at least one structural portion formed of metal; and
a polymer body at least partially surrounding the at least one structural portion,
wherein the polymer body defines an overall shape of the bone fixation implant comprising the overall width, the overall length, and an overall thickness,
wherein the polymer body defines the openings, such that direct contact between the metal of the structural portion and the attachment member is prevented, and
wherein the polymer body defines the bone-engaging surface, the muscle or soft tissue-engaging surface, and the eyelets such that direct contact between the metal of the structural portion and any of the bone structure, the muscle or soft tissue structure, or sutures is prevented.

11. The method of claim 1, wherein the bone fixation implant comprises polyether ether ketone (PEEK).

12. The method of claim 1, wherein the bone fixation implant comprises:
at least one structural portion formed of metal; and
a polymer body at least partially surrounding the at least one structural portion,
wherein the polymer body defines an overall shape of the bone fixation implant comprising the overall width, the overall length, and an overall thickness,
wherein the polymer body defines the openings, such that direct contact between the metal of the structural portion and the attachment member is prevented, and
wherein the polymer body defines the bone-engaging surface and the muscle or soft tissue-engaging surface such that direct contact between the metal of the structural portion and any of the bone structure or the muscle or soft tissue structure is prevented.

13. The method of claim 12, wherein the polymer body comprises polyether ether ketone (PEEK).

14. The method of claim 12, wherein the structural portion comprises at least one of titanium, aluminum, stainless steel, or Nitinol.

15. The method of claim 12, wherein the structural portion comprises at least one of a wire, a plate, or a mesh.

16. The method of claim 1, wherein:
at least one of the bone-engaging surface or the muscle or soft tissue-engaging surface defines a texture configuration, and
the texture configuration of the bone-engaging surface or the muscle or soft tissue-engaging surface enhances engagement of the bone fixation implant with the underlying bone structure or the overlying muscle or soft tissue structure, respectively.

* * * * *